US012657629B2

(12) United States Patent
Choi

(10) Patent No.: US 12,657,629 B2
(45) Date of Patent: Jun. 16, 2026

(54) DECISION-MAKING METHOD USING ARTIFICIAL INTELLIGENCE MODEL, SERVER, AND COMPUTER PROGRAM

(71) Applicant: Han Chul Choi, Seongnam-si (KR)

(72) Inventor: Han Chul Choi, Seongnam-si (KR)

( * ) Notice: Subject to any disclaimer, the term of this patent is extended or adjusted under 35 U.S.C. 154(b) by 102 days.

(21) Appl. No.: 18/292,348

(22) PCT Filed: Jul. 15, 2022

(86) PCT No.: PCT/KR2022/010352
§ 371 (c)(1),
(2) Date: Jan. 26, 2024

(87) PCT Pub. No.: WO2023/018037
PCT Pub. Date: Feb. 16, 2023

(65) Prior Publication Data
US 2024/0289878 A1      Aug. 29, 2024

(30) Foreign Application Priority Data
Aug. 10, 2021      (KR) ........................ 10-2021-0105095

(51) Int. Cl.
*G06Q 40/04* (2012.01)
*A61B 5/1455* (2006.01)
*A61B 5/372* (2021.01)

(52) U.S. Cl.
CPC ........... *G06Q 40/04* (2013.01); *A61B 5/1455* (2013.01); *A61B 5/372* (2021.01)

(58) Field of Classification Search
CPC ..................................................... G06Q 40/04
See application file for complete search history.

(56) References Cited

U.S. PATENT DOCUMENTS

| | | | | |
|---|---|---|---|---|
| 2011/0298706 A1* | 12/2011 | Mann | ...................... | H03K 17/94 |
| 2019/0295169 A1 | 9/2019 | Nazari et al. | | |
| 2020/0184496 A1* | 6/2020 | Medanic | ................ | G06Q 30/02 |
| 2021/0342836 A1* | 11/2021 | Cella | ...................... | G06Q 20/40 |

FOREIGN PATENT DOCUMENTS

| | | | | | |
|---|---|---|---|---|---|
| CA | 3013959 | * | 8/2017 | ............. | A61B 5/145 |
| CA | 3174397 | * | 12/2021 | ............. | A61B 5/369 |
| FR | 3174397 | * | 12/2021 | .............. | A61B 5/16 |

(Continued)

OTHER PUBLICATIONS

Torres et al., in "Machine Learning Analysis of EEG Measurements of Stock Trading Performance," from Advances in Intelligent Systems and Computing, 2020 (Year: 2020).*

*Primary Examiner* — Mike Anderson
*Assistant Examiner* — Brandon M Duck
(74) *Attorney, Agent, or Firm* — INVENSTONE PATENT, LLC

(57) ABSTRACT

Provided are: a decision-making method using an artificial intelligence model, a server, and a computer program. A decision-making method using an artificial intelligence model according to various embodiments of the present invention comprises the steps of: acquiring a transaction request for a financial product from a trader; determining a processing mode for the acquired transaction request based on data about the trader, and outputting a transaction signal corresponding to the determined processing mode for the transaction request.

14 Claims, 8 Drawing Sheets

(56)          References Cited

FOREIGN PATENT DOCUMENTS

| KR | 10-2001-0091838 A | 10/2001 | |
|----|-------------------|---------|---|
| KR | 10-2001-0098355 A | 11/2001 | |
| KR | 10-2018-0117800 A | 10/2018 | |
| KR | 10-2009309 A | 8/2019 | |
| KR | 10-2368638 A | 2/2022 | |
| WO | WO 2019223880 | * 11/2019 | ........... A61B 5/1455 |

* cited by examiner

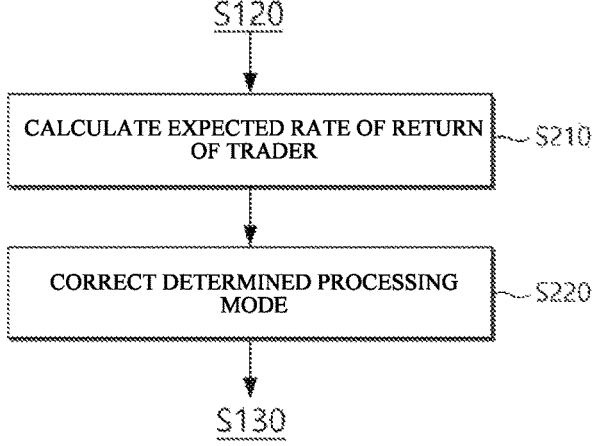

TRANSACTION REQUEST 200-1
MULTI-DIMENSIONAL MATRIX DATA

TRANSACTION REQUEST 200-2
MULTI-DIMENSIONAL MATRIX DATA

TRANSACTION REQUEST 200-3
MULTI-DIMENSIONAL MATRIX DATA

100

MULTI-DIMENSIONAL MATRIX DATA

ARTIFICIAL INTELLIGENCE MODEL

TRANSACTION REQUEST

200-N
MULTI-DIMENSIONAL MATRIX DATA

TRANSACTION SIGNAL
- PROCESS TRANSACTION ORDER AS REQUESTED ACCORDING TO TRANSACTION REQUEST
- PROCESS TRANSACTION ORDER TO BE OPPOSITE TO TRANSACTION REQUEST
- PROCESS TRANSACTION REQUEST TO STAND BY

CALCULATE EXPECTED RATE OF RETURN OF TRADER    S210

CORRECT DETERMINED PROCESSING MODE    S220

DECISION-MAKING METHOD USING ARTIFICIAL INTELLIGENCE MODEL, SERVER, AND COMPUTER PROGRAM

CROSS-REFERENCE TO RELATED APPLICATIONS

This application is a National Stage filing under 35 U.S.C. 371 of International Application No. PCT/KR2022/010352 filed on Jul. 15, 2022, which claims the benefit of earlier filing date and right of priority to Korean Application No. 10-2021-0105095, filed on Aug. 10, 2021, in the Korean Intellectual Property Office, the contents of which are all hereby incorporated by reference herein in their entirety.

TECHNICAL FIELD

Various embodiments of the present invention relate to a decision-making method using an artificial intelligence model, a server, and a computer program.

BACKGROUND ART

Investing in financial products, such as stocks, bonds, raw materials, foreign exchange, and derivatives may significantly increase assets, but unlike deposits or savings, the principal is not guaranteed, and the assets are most likely to be reduced.

A trader (a financial transaction responsible person) refers to a person who brokers transactions between customers while trading with his or her position or predicting prices at the time of transaction of a financial product. That is, the trader is a job that makes profits by buying and selling financial products, such as stocks, bonds, and derivatives using financial tools. The trader mainly buys and sells securities for the purpose of profiting from short-term stock price fluctuations. Therefore, the trader does not hold the financial products for a long time but looks for financial products that are likely to rise in the short time and trades them over a short period of time.

The trader analyzes and figures out global financial and economic information using various communication media and materials such as news or broadcasting. The trader executes the transaction after determining the impact of the information they have learned on the market.

Further, the trader reviews product price trends, financial statements, economic indicators, financial data, results of quantitative analysis models, and news that are useful for transaction. The trader is allocated with position limits (a transaction amount assigned per person) for fund management from the fund management department. The trader determines the transaction strategy, mode, and timing, and places a transaction order using a transaction order system.

Therefore, the financial product transaction as the trader is the result of the entry timing and the liquidation timing (a long-term or short-term result of the derivatives) and it is important to keep a cool-headed mind at this timing in accordance with one's rules. Accordingly, when the trader succeeds in the financial product transaction, it means that the trader overcomes oneself, understands the minds of other market participants and a current timing to catch a good timing for the transaction.

However, since the trader is also a human, each trader's physical or mental state may easily affect the decision to trade the financial product. If the trader is in a bad condition and makes wrong or somewhat impulsive decisions, the trader may incorrectly trade the financial product, resulting in large losses. For example, the trader may incur a large loss by buying a financial product even though it is a clear selling timing or does not make a profit by selling the financial product even though it is a clear buying timing.

SUMMARY

An object to be achieved by the present invention is to provide a financial product transaction method, a server, and a computer program that considers the trader's physical or mental condition interferes with the trader's correct judgement. The present invention is to provide a financial product transaction method, a server, and a computer program for trading financial products using an artificial intelligence model that uses various data, including biodata, to derive new trading signals. The present invention is to provide a financial product transaction method, a server, and a computer program that diagnoses a state using the trader's bio information at a corresponding point in time when a trading order request is obtained from a trader and determines a method of processing a trading order request according to the diagnosis result. Accordingly, the present invention can prevent incorrect trading requests due to the trader's personal situation or state, or modify the trading direction to maximize profits.

Technical problems of the present invention are not limited to the above-mentioned technical problems, and other technical problems, that are not mentioned above, can be clearly understood by those skilled in the art from the following descriptions.

In order to achieve the above-described object, a financial product transaction method using an artificial intelligence model according to an embodiment of the present invention may include the steps of: acquiring a transaction request for a financial product from a trader; determining a processing mode for the acquired transaction request based on data about the trader; and outputting a transaction signal corresponding to the determined processing mode for the transaction request.

In various embodiments, the data about the trader includes biodata including at least one of electroencephalography (EEG) data measured by an electroencephalography sensor and brain oxygen saturation data measured by a functional near-infrared spectroscopy (fNIRS) sensor, and the step of determining a processing mode for the acquired transaction request may include: a step of determining the processing mode for the acquired transaction request by analyzing data about the trader by means of a previously trained artificial intelligence model.

In various embodiments, the step of determining a processing mode for the acquired transaction request by analyzing data about the trader may include: a step of extracting result data about the processing mode for the acquired transaction request by inputting biodata about the trader collected for a predetermined period in the past, as of the time when the transaction request for the financial product is acquired from the trader, to the previously trained artificial intelligence model—the previously trained artificial intelligence model is trained with biodata at the time when each of the plurality of traders transmits a transaction request, a transaction signal output according to the transaction request of each of the plurality of traders, and a rate of return according to the output transaction signal as learning data—as input data.

In various embodiments, the step of determining a processing mode for the acquired transaction request by analyzing data about the trader may include: a step of extracting result data about a state of the trader by inputting biodata about the trader collected for a predetermined period in the past, as of the time when the transaction request for the financial product is acquired from the trader, to the previously trained artificial intelligence model as input data; and a step of determining a processing mode for the acquired transaction request based on the state of the trader, wherein the previously trained artificial intelligence model is trained with biodata according to a state of each of the plurality of traders as learning data.

In various embodiments, the data about the trader further includes transaction history data including test result data about tests conducted on the trader before the opening of the financial product market, and at least one of the trader's past financial product transaction data, rate of return data, and trader's personal information data, and the step of determining a processing mode for the acquired transaction request by analyzing data about the trader may include: a step of extracting result data about the processing mode for the acquired transaction request by inputting at least one data of the transaction history data and the test result data and the biodata to the previously trained artificial intelligence model as input data.

In various embodiments, the step of determining a processing mode for the acquired transaction request by analyzing data about the trader may include: a step of extracting result data about the processing mode for the acquired transaction request by inputting financial data—the financial data includes at least one of technical indicators, financial statements, performance, news, and chart patterns—and the biodata about the trader to the previously trained artificial intelligence model as input data.

In various embodiments, the step of determining a processing mode for the acquired transaction request by analyzing data about the trader may include: a step of calculating a probability of price increase of the financial product using biodata collected from the plurality of traders for a predetermined period from a time when the information about the financial product is provided to the plurality of traders; and a step of correcting the determined processing mode for the transaction request, based on the calculated probability of price increase of the financial product.

In various embodiments, the step of determining a processing mode for the acquired transaction request by analyzing data about the trader may include: a step of calculating an expected rate of return of the trader using at least one data of the biodata about the trader, the transaction history data, the test result data, and the financial data, and correcting the determined processing mode for the transaction request based on the calculated expected rate of return, wherein the transaction history data includes at least one of the trader's past financial product transaction data, the rate of return data, and the trader's personal information data, wherein the test result data is a result data for conducted on the trader before the opening of the financial product market, wherein the financial data includes at least one of technical indicators, financial statements, performance, news, and chart patterns.

In various embodiments, the data about the trader includes biodata including at least one of electroencephalography (EEG) data measured by an electroencephalography sensor and brain oxygen saturation data measured by a functional near-infrared spectroscopy (fNIRS) sensor, and the step of determining a processing mode for the acquired transaction request may include: a step of collecting biodata from the plurality of traders for a predetermined period from a time when the information about the financial product is provided to the plurality of traders; a step of extracting result data about the probability of price increase of the financial product by generating multi-dimensional matrix data using the collected biodata of the plurality of traders and inputting the generated multi-dimensional matrix data to a previously trained artificial intelligence model as input data; and a step of determining the processing mode for the acquired transaction request using the probability of price increase of the financial product, wherein the previously trained artificial intelligence model is a model trained with information about a plurality of financial products, a plurality of biodata collected from the plurality of traders at the time when the information about the plurality of financial products is provided, a plurality of multi-dimensional matrix data generated using the plurality of biodata, and a price change amount of the plurality of financial products as learning data.

In various embodiments, the step of determining the processing mode for the acquired transaction request using the probability of price increase of the financial product may include: a step of correcting the determined processing mode for the transaction request using biodata about the trader collected for a predetermined period in the past, as of the time when the transaction request for the financial product is acquired from the trader.

In various embodiments, the step of correcting the determined processing mode for the transaction request may include: a step of extracting result data about a state of the trader by inputting biodata about the trader for a predetermined period in the past, as of the time when the transaction request for the financial product is acquired from the trader, to the previously trained artificial intelligence model as input data, and a step of correcting the determined processing mode for the transaction request based on the state of the trader, wherein the previously trained artificial intelligence model is a model trained with biodata according to a state of each of the plurality of traders as learning data.

In various embodiments, the step of collecting biodata from the plurality of traders includes: a step of providing information about occurred event to the plurality of traders in response to the sensing of the occurrence of the event about the financial product and collecting biodata from the plurality of traders for a predetermined period from a time that the information about the occurred event is provided to the plurality of traders, and the step of determining the processing mode for the acquired transaction request using the probability of price increase of the financial product may include: a step of determining an attribute of the occurred event using the collected biodata of the plurality of traders and correcting the determined processing mode for the transaction request based on the determined attribute.

In various embodiments, the data about the trader includes biodata including at least one of electroencephalography (EEG) data measured by an electroencephalography sensor and brain oxygen saturation data measured by a functional near-infrared spectroscopy (fNIRS) sensor, transaction history data including at least one of trader's past financial product transaction data, rate of return data, and trader's personal information data, and test result data about tests conducted on the trader before the opening of the financial product market, the step of acquiring the transaction request for the financial product includes: a step of simultaneously acquiring the transaction request for the financial product from a plurality of traders at a predetermined time, and the step of determining a processing mode for the acquired transaction request includes: a step of collecting biodata from the plurality of traders for a predetermined period from a time when the information about the financial product is provided to the plurality of traders; a step of extracting result data about a probability of price increase of the financial product by generating multi-dimensional matrix data using at least one of the collected biodata of the plurality of traders, a transaction request for the financial product that is simultaneously acquired from the plurality of traders, the transaction history data, and the test result data and inputting the generated multi-dimensional matrix data to the previously trained artificial intelligence model as input data; and a step of determining the processing mode for the transaction request for the financial product that is simultaneously acquired from the plurality of traders using the probability of price increase of the financial product.

In various embodiments, the outputting of the transaction signal may include: a step of calculating a buying request probability and a selling request probability of each of the plurality of traders for a first financial product using data about each of the plurality of traders; and a step of automatically outputting a transaction signal for the first financial product using the calculated buying request probability and the calculated selling request probability.

In various embodiments, the step of automatically outputting the transaction signal includes: a step of determining a weight to be assigned to each of the plurality of traders based on a rate of return according to a first transaction signal output using first data about each of the plurality of traders; and a step of outputting a second transaction signal using second data about each of the plurality of traders, the determined weight being assigned to the selling request probability and the buying request probability calculated using the second data and the second transaction signal being automatically output using the buying request probability assigned with the weight and the selling request probability assigned with the weight.

In order to achieve the above-described object, a financial product transaction server using an artificial intelligence model according to another embodiment of the present invention may include: a processor; a network interface; a memory; and a computer program that is loaded in the memory and is executed by the processor, and the computer program includes: an instruction that acquiring a transaction request for a financial product from a trader; an instruction that determining a processing mode for the acquired transaction request based on data about the trader; and an instruction outputting a transaction signal corresponding to the determined processing mode for the transaction request.

In order to achieve the above-described object, a computer program recorded in a computer readable recording medium according to another embodiment of the present invention may be stored in a computer readable recording medium to be coupled to a computing device to execute the steps of: acquiring a transaction request for a financial product from a trader; determining a processing mode for the acquired transaction request based on data about the trader; and outputting a transaction signal corresponding to the determined processing mode for the transaction request.

Other detailed matters of the embodiments are included in the detailed description and the drawings.

According to various embodiments of the present invention, a method of trading financial products can consider that the trader's physical and mental state interferes with the trader's correct judgment.

According to various embodiments of the present invention, when a purchase and sale request is obtained from a trader, the financial product trading method may determine a method of processing the purchase and sale request according to the diagnosis result by diagnosing the state using the trader's bio information at the time point.

According to various embodiments of the present invention, the financial product trading method has the advantage of preventing incorrect sales requests due to a trader's personal situation or condition, modifying the sales direction to maximize profits, or deriving a new sales signal.

Further, the financial product trading method can consider not only the biodata about the trader, but also transaction history data, test (for example, test conducted on the trader) result data, and financial data. the financial product trading method has the advantageous of being able to judge the appropriateness more accurately by considering these data and determining the appropriateness of the trading request obtained from the trader.

The effects of the present invention are not limited to the technical effects mentioned above, and other effects that are not mentioned can be clearly understood by those skilled in the art from the following description.

BRIEF DESCRIPTION OF THE DRAWINGS

FIG. 5 is a view illustrating a process of performing a financial product transaction method for a plurality of traders according to a first embodiment, in various exemplary embodiments.

FIG. 6 is a flowchart for explaining a method of correcting a processing mode for a transaction request based on an expected rate of return of a trader, in various exemplary embodiments.

DETAILED DESCRIPTION OF THE EMBODIMENT

Figure 1:
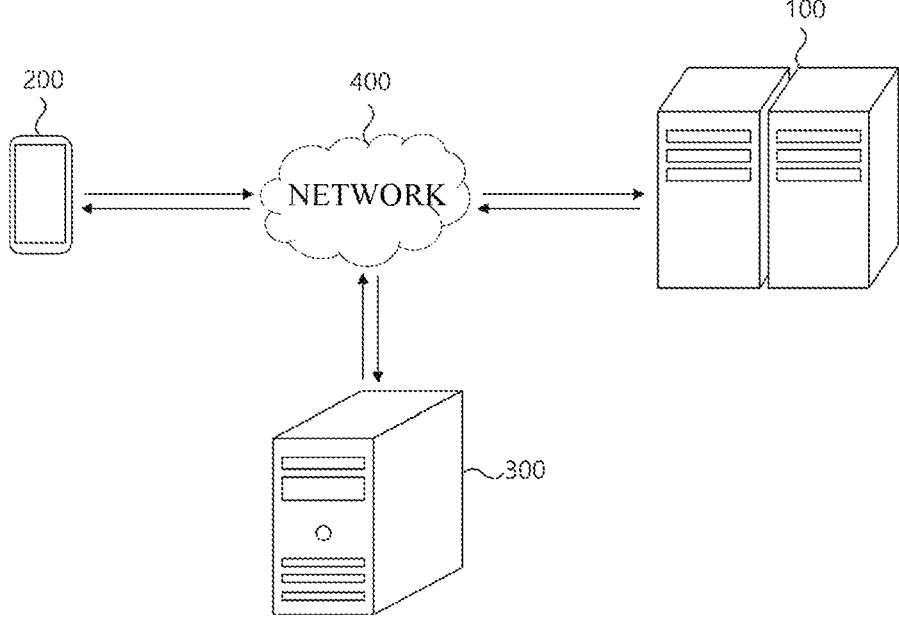
FIG. 1 is a view illustrating a financial product transaction system using an artificial intelligence model according to an exemplary embodiment of the present invention.

Advantages and characteristics of the present invention and a method for achieving the advantages and characteristics will be clear by referring to preferable embodiments described below in detail together with the accompanying drawings. However, the present disclosure is not limited to exemplary embodiments disclosed herein but will be implemented in various different forms. The exemplary embodiments are provided by way of example only so that a person of ordinary skilled in the art may fully understand the disclosures of the present invention and the scope of the present invention. Therefore, the present disclosure will be defined only by the scope of the appended claims.

The terms used in the present specification are for explaining the embodiments rather than limiting the present invention. Unless particularly stated otherwise in the present specification, a singular form also includes a plural form. The term "comprise" and/or "comprising" used in the specification does not exclude the presence or addition of one or more other components in addition to the mentioned component. Like reference numerals generally denote like elements throughout the specification and "and/or" includes each of mentioned components and all combinations of one or more components. Although the terms "first", "second", and the like are used for describing various components, these components are not confined by these terms. These terms are merely used for distinguishing one component from the other components. Therefore, a first component to be mentioned below may be a second component in a technical spirit of the present invention.

Unless otherwise defined, all terms (including technical and scientific terms) used in the present specification may be used as the meaning that may be commonly understood by the person with ordinary skill in the art, to that the present invention belongs. Further, it will be further understood that terms defined in commonly used dictionaries should not be interpreted in an idealized or excessive sense unless expressly and specifically defined.

The term "~unit" or "~module" used in the specification refers to a software, or a hardware component such as FPGA or ASIC and the "unit" or "module" performs some functions. However, "~unit" or "~module" is not limited to the software or the hardware. "~unit" or "~module" may be configured to be in an addressable storage medium or may be configured to reproduce one or more processors. Accordingly, as an example, "~unit" or "~module" includes components such as software components, object-oriented software components, class components, and task components, processes, functions, attributes, procedures, subroutines, segments of a program code, drivers, a firmware, a microcode, a circuit, data, database, data structures, tables, arrays, and variables. A function that is provided in the components and "~units" or "~modules" may be combined with a smaller number of components and "~units" or "~modules" or divided into additional components and "~units" or "~modules".

Spatially relative terms such as "below", "beneath", "lower", "above", or "upper" may be used to easily describe the correlation between one component and other components as illustrated in the drawings. The spatially relative terms should be understood to include different directions of the elements when the elements are used or operated in addition to the direction illustrated in the drawings. For example, when the component illustrated in the drawing is turned over, a component that is disposed "below" or "beneath" other component may be disposed "above" other component. Accordingly, the exemplarily term "below" or "beneath" may include both downward and upward directions. The components may be oriented in different directions so that terms that are spatially relative may be interpreted according to the orientation.

In the present disclosure, a computer refers to all types of hardware device including at least one processor and depending on the exemplary embodiment, is understood to include a software configuration that operates in the corresponding hardware device. For example, the computer may be understood to include all smartphones, tablet PCs, desktops, notebooks, and user clients and applications run in each device, but is not limited thereto.

Further, in the specification, it is described that a transaction request for a financial product is obtained from a plurality of traders and the appropriateness thereof is determined to determine the processing mode for the transaction request (for example, buying/selling order or long/short order), rather than selecting a profitable financial product having a good rate of return, buying the selected financial product, or recommending information about the selected financial product. However, the invention is not limited thereto and the transaction requests for the financial product are acquired from the plurality of traders and the appropriateness thereof is determined and when it is determined to be appropriate, a type of stocks may be recommended to the other traders or general customers.

Further, in the present specification, it is basically described that the appropriateness for the transaction requests acquired from the plurality of traders is determined, but the invention is not limited thereto. The invention is applied to the transaction request acquired from the general customer in the same way.

Hereinafter, exemplary embodiments of the present disclosure will be described in detail with reference to the accompanying drawings.

Steps described in the present disclosure are described to be performed by a computer, but a subject of each step is not limited thereto and at least some of the steps may be performed in different devices according to the embodiments.

FIG. 1 is a view illustrating a financial product transaction system using an artificial intelligence model according to an exemplary embodiment of the present invention.

Referring to FIG. 1, the financial product transaction system using an artificial intelligence model according to an embodiment of the present invention may include a financial product transaction server 100, a trader terminal 200, and an external server 300.

Here, the financial product transaction system using an artificial intelligence model illustrated in FIG. 1 is according to one embodiment and a component thereof is not limited to the embodiment illustrated in FIG. 1 and may be added, changed, or deleted if necessary.

In one embodiment, the financial product transaction server 100 may acquire a transaction request for a specific financial product from a trader. The financial product transaction server 100 may determines a processing mode for the transaction request to output a transaction signal to perform the transaction for the specific financial product. For example, the financial product transaction server 100 decides an appropriateness of a transaction request acquired from the trader (or the trader terminal 200), determines a processing mode for the acquired transaction request based on the decided appropriateness. The financial product transaction server 100 may output a transaction signal (for example, a buying signal, a selling signal, or a stand-by signal) corresponding to the determined processing mode.

In various embodiments, the financial product transaction server 100 does not acquire a separate transaction request from the trader but analyzes data about the trader to automatically output a transaction signal. That is, the financial product transaction server 100 outputs a transaction signal aimed at improving a rate of return even without receiving a separate instruction, to perform the transaction for the financial product.

In various embodiments, the financial product transaction server 100 has the same hardware configuration as a general web server and includes a program module that is implemented by various types of languages, such as Python, C, C++, Java, Visual Basic, or Visual C, to perform various functions as software.

Further, the financial product transaction server 100 may be implemented in hardware for general servers using various web server programs provided according to an operation system, such as DOS, windows, Linux, Unix, or Macintosh.

In various embodiments, the financial product transaction server 100 is connected to the trader terminal 200 through the network 400. The financial product transaction server 100 may provide an application for financial product transaction to the trader terminal 200.

Here, the network may refer to a connection structure allowing information exchange between nodes, such as trader terminals 200 of a plurality of traders and the financial product transaction server 100. For example, the network 400 includes a local area network (LAN), a wide area network (WAN), Internet (WWW; world wide web), a wired/wireless data communication network, a telephone network, a wired/wireless television communication network.

Further, the wireless data communication network includes 3G, 4G, 5G, $3^{rd}$ generation partnership project (3GPP), $5^{th}$ generation partnership project (5GPP), long term evolution (LTE), world interoperability for microwave access (WIMAX), Wi-Fi, Internet, local area network (LAN), wireless local area network (Wireless LAN), wide area network (WAN), personal area network (PAN), radio frequency (RF), Bluetooth network, near-field communication (NFC) network, satellite broadcasting network, analog broadcasting network, and digital multimedia broadcasting network (DMB), but is not limited thereto.

In one embodiment, the trader terminal 200 may be connected to the financial product transaction server 100 through the network 400. The trader terminal 200 may provide data (for example, biodata, test result data, etc.) for deciding the appropriateness for the transaction request together with the transaction request for a specific financial product to the financial product transaction server 100. To this end, the trader terminal 200 may include a sensor module collecting biodata but is not limited thereto. The trader terminal 200 may be implemented to be connected to a sensor module that is separately provided at the outside of the trader terminal 200 in a wired/wireless mode.

In various embodiments, the trader terminal 200 may be a smartphone including an operation system that may drive an application and downloads, installs, and executes the application provided by the financial product transaction server 100 to trade the financial product. However, the trader terminal 200 is not limited thereto, but may include all kinds of handheld wireless communication devices that ensure portability and mobility, such as a navigation, a personal communication system (PCS), a global system for mobile communication (GSM), a personal digital cellular (PDC), a personal handyphone system (PHS), a personal digital assistant (PDA), an international mobile communication (IMT)-2000, code division multiple access (CDMA)-2000, W-code division multiple access (W-CDMA), a wireless broadband internet (Wibro) terminal, a smart pad, and a tablet PC.

In one embodiment, the external server 300 may be connected to the financial product transaction server 100 through the network 400. The external server 300 is provided with a transaction signal output from the financial product transaction server 100 to process the transaction for the financial product. For example, the external server 300 may be a securities company server or a home trading system (HTS) server.

In various embodiments, the external server 300 stores and manages various information/data (for example, transaction history data, financial data, data related to a financial product, etc.) required for the financial product transaction server 100 to trade the financial product. The external server 300 may store and manage various information/data generated in accordance with the financial product transaction. For example, the external server 300 may be a storage server that is separately provided at the outside of the financial product transaction server 100 but is not limited thereto. Hereinafter, a hardware configuration of the financial product transaction server 100 will be described with reference to FIG. 2.

Figure 2:
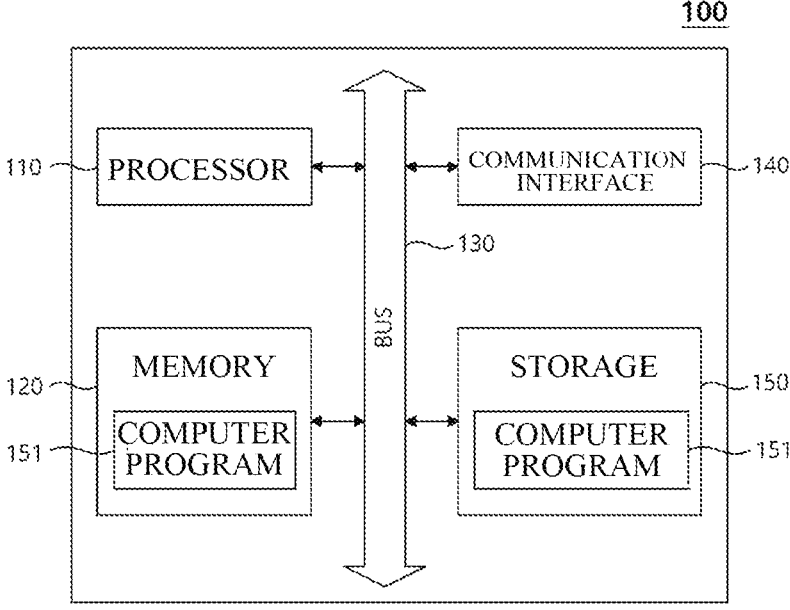
FIG. 2 is a diagram of a hardware configuration of a financial product transaction server using an artificial intelligence model according to another exemplary embodiment of the present invention.

FIG. 2 is a diagram of a hardware configuration of a financial product transaction server using an artificial intelligence model according to another exemplary embodiment of the present invention.

Referring to FIG. 2, a financial product transaction server 100 (hereinafter, a computing device 100) according to another embodiment of the present disclosure may include one or more processors 110, a memory 120 that loads a computer program 151 executed by the processor 110, a bus 130, a communication interface 140, and a storage 150 that stores the computer program 151. Here, in FIG. 2, only components related to the embodiment of the present invention are illustrated. Accordingly, those skilled in the art to that the present invention pertains may understand that general-purpose components may be included other than the components illustrated in FIG. 2.

The processor 110 controls the overall operation of each configuration of the computing device 100. The processor 110 may be configured to include a central processing unit (CPU), a microprocessor unit (MPU), a micro controller unit (MCU), a graphic processing unit (GPU), or an arbitrary processor that is well known in the technical field of the present invention.

Further, the processor 110 may perform a computation for at least one application or program to execute the method according to the embodiments of the present invention and the computing device 100 may include one or more processors.

In various embodiments, the processor 110 may further include a random-access memory (RAM, not illustrated) and a read-only memory (ROM, not illustrated) that transitorily and/or permanently store a signal (or data) processed in the processor 100. Further, the processor 110 may be implemented in the form of a system on chip (SoC) including at least one of a graphic processor, an RAM, and a ROM.

The memory 120 stores various data, instructions and/or information. The memory 120 may load one or more computer programs 151 from the storage 150 to execute the operation/method according to various embodiments of the present invention. When the computer program 151 is loaded in the memory 120, the processor 110 executes one or more instructions that configure the computer program 151 to perform the method/operation. The memory 120 may be implemented by a volatile memory, such as RAM, but the technical scope of the present disclosure is not limited thereto.

The bus 130 provides a communication function between components of the computing device 100. The bus 130 may be implemented by various types of buses, such as an address bus, a data bus, and a control bus.

The communication interface 140 supports the wired/wireless Internet communication of the computing device 100. Further, the communication interface 140 may support various communication methods other than the Internet communication. To this end, the communication interface 140 may include a communication module that is well-known in the technical field of the present invention. In some embodiments, the communication interface 140 may be omitted.

The storage 150 may non-temporarily store the computer program 151. When the financial product transaction process using the artificial intelligence model is performed by the computing device 100, the storage 150 may store various information required to provide the financial product transaction process using the artificial intelligence model.

The storage 150 may be configured by including a non-volatile memory such as a read only memory (ROM), an erasable programmable ROM (EPROM), an electrically erasable programmable ROM (EEPROM), and a flash memory, a hard disk, a removable disk or any computer readable recording medium that is well known in the technical field of the present invention.

The computer program 151 may include one or more instructions to allow the processor 110 to perform methods/operations according to various embodiments of the present invention when it is loaded in the memory 120. That is, the processor 110 executes one or more instructions to perform the methods/operations according to various embodiments of the present invention.

In one embodiment, the computer program 151 may include one or more instructions to perform a financial product transaction method using an artificial intelligence model including the steps of acquiring a transaction request for a financial product from a trader, determining a processing mode for the acquired transaction request based on data about the trader, and outputting a transaction signal corresponding to the determined processing mode for the transaction request.

Steps of the method or algorithm described in connection with the exemplary embodiment of the present invention may be directly implemented by hardware or implemented by a software module executed by the hardware or a combination thereof. The software module may reside on RAM (Random Access Memory), ROM (Read Only Memory), EPROM (Erasable Programmable ROM), EEPROM (Electrically Erasable Programmable ROM), a flash memory, a hard disk, a removable disk, a CD-ROM, or an arbitrary computer readable recording medium that is well-known in the technical field of the present invention.

Components of the present invention is implemented as a program (or an application) to be coupled to a computer that is hardware to be executed to be stored in a medium. The components of the present invention may be executed with software programming or software elements, and similar to this, the embodiment may be implemented by programming or scripting languages such as C, C++, Java, or assembler including various algorithms implemented by a combination of data structures, processes, routines, or other program configurations. The functional aspects may be implemented by an algorithm executed in one or more processors.

Hereinafter, the financial product transaction method using an artificial intelligence model according to various embodiments performed by the computing device 100 will be described. First, a financial product transaction method using an artificial intelligence model according to a first embodiment will be described with reference to FIGS. 3 to 8.

Figure 3:
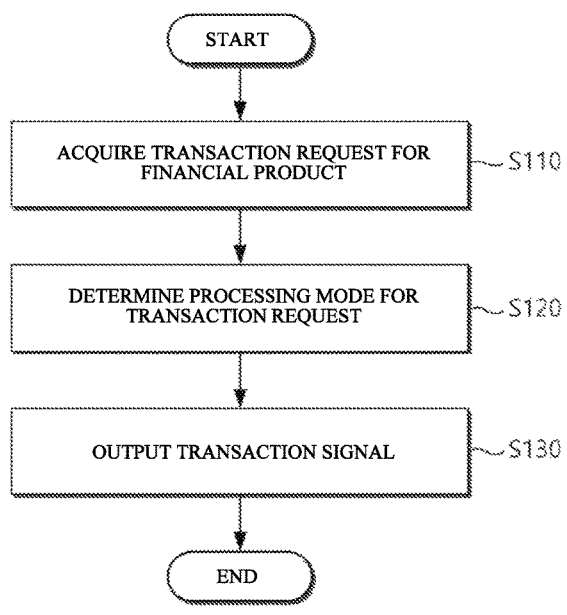
FIG. 3 is a flowchart for explaining a first embodiment of a financial product transaction method using an artificial intelligence model according to still another exemplary embodiment of the present invention.
Figure 4:
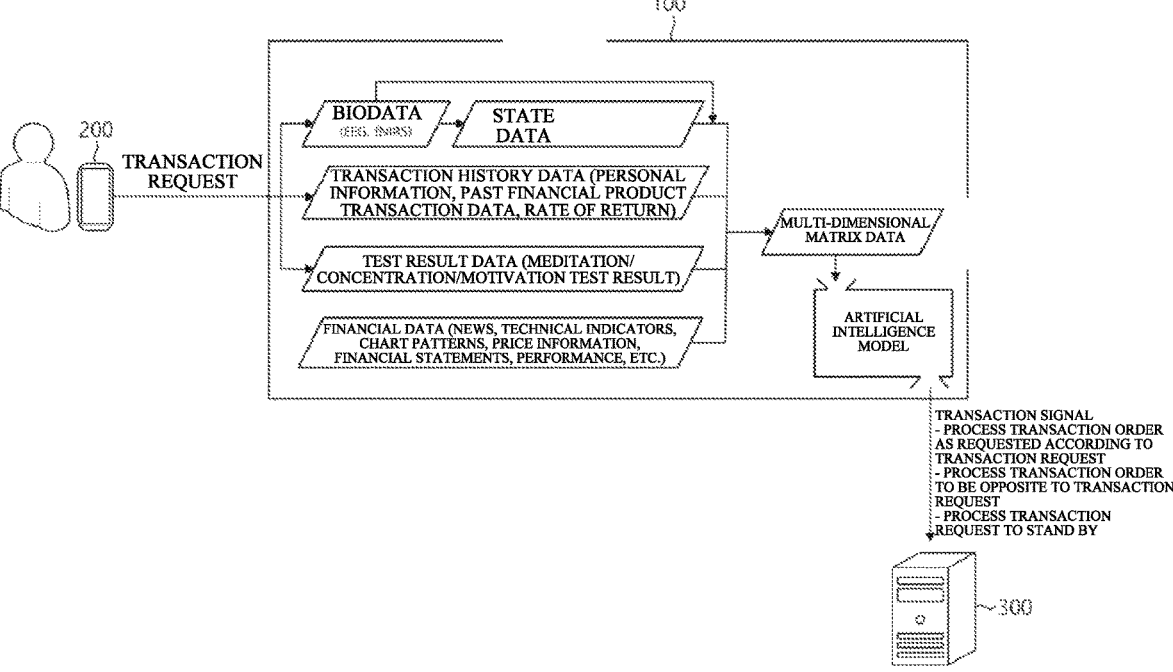
FIG. 4 is a view illustrating a process of performing a financial product transaction method for one trader according to a first embodiment, in various exemplary embodiments.

FIG. 3 is a flowchart for explaining a first embodiment of a financial product transaction method using an artificial intelligence model according to still another exemplary embodiment of the present invention, FIG. 4 is a view illustrating a process of performing a financial product transaction method for one trader according to a first embodiment, in various exemplary embodiments, and FIG. 5 is a view illustrating a process of performing a financial product transaction method for a plurality of traders according to a first embodiment, in various exemplary embodiments.

Here, it is described that a financial product transaction method using an artificial intelligence model of FIGS. 3 to 5 is performed by a computing device 100 but is not limited thereto. The financial product transaction method may be independently performed in a trader terminal 200 as the trader terminal 200 executes software provided from the computing device 100.

Referring to FIGS. 3 to 5, in step S110, the computing device 100 may acquire a transaction request for a financial product from a trader.

In various embodiments, the computing device 100 may be connected to the trader terminal 200 through the network 400 to provide a user interface UI (for example, a graphic user interface; GUI) that outputs information about a plurality of financial product (for example, a financial product name, an opening price, a high price, a low price, a previous day's closing price, a foreign buying volume, an institutional buying volume, a upper limit price, a lower limit price, a chart, news about a financial product, etc.) to the trader terminal 200. The computing device 100 may receive a buying or selling request for a specific financial product from the trader through the UI.

Here, the buying request is a request to buy a financial product selected by the trader and may include a quantity and price information of financial products to be bought but is not limited thereto.

Further, the selling request is a request to sell any one financial product among a plurality of financial products held by the trader. The selling request may include a quantity and price information of the financial product to be sold but is not limited thereto.

In step S120, the computing device 100 may determine a processing mode for the acquired transaction request based on data about the trader.

Here, data about the trader may include biodata including at least one of electroencephalography (EEG) data measured by an electroencephalography sensor and brain oxygen saturation data measured by a functional near-infrared spectroscopy (fNIRS) sensor. However, the data is not limited thereto and the biodata further may include other general sensor data (for example, heart rate data, respiratory rate data, or blood flow data) that may be utilized to determine the trader's state.

Further, the biodata may further include not only primary biodata about the trader, that is collected by a sensor module, but also secondary biodata (for example, a trader's concentration level, a stress level, and a risk taking tendency) that is generated by processing the primary biodata.

Further, here, it is described that at least one of EEG data and oxygen saturation data of the brain is used to decide the state of the trader or determine a processing mode for the transaction request acquired from the trader. However, more accurate decision may be made by using both EEG data and oxygen saturation data of the brain, rather than using only any one of EEG data and oxygen saturation data of the brain so that it is desirable to use EEG data and oxygen saturation data of the brain together (for example, see "Mental stress assessment using simultaneous measurement of EEG and fNIRS", Al-Shargie, F., Kiguchi, M., Badruddin, N., Dass, S. C., Hani, A. F. M., & Tang, T. B. (2016), Biomedical optics express, 7(10), 3882-3898.).

However, when only one of EEG data and oxygen saturation data of the brain may be selectively used in some cases, the EEG data may be considered as a top priority by setting the EEG data as a default.

Further, here, the data about the trader may further include data other than the biodata. For example, the transaction history data including at least one of the trader's past financial product transaction data, rate of return data, and trader's personal information data, and test result data about tests conducted on the trader before the opening of the financial product market. But, the data about the trader is not limited thereto.

In various embodiments, the computing device 100 is connected to the trader terminal 200 (for example, a wearable device including a plurality of sensors) to obtain EEG data and oxygen saturation data of the brain through a sensor that is separately provided in the trader terminal 200.

In various embodiments, the computing device 100 may determine a processing mode for the acquired transaction request using biodata about the trader and a previously trained artificial intelligence model.

Here, the previously trained artificial intelligence model (for example, a first artificial intelligence model) may be a model that is trained with biodata at the time when each of the plurality of traders transmits a transaction request, a transaction signal output in accordance with the transaction request of each of the plurality of traders, and a rate of return according to the output transaction signal, as learning data. For example, the first artificial intelligence model may be a recurrent neural network (RNN) model but is just an example mentioned to more easily describe an artificial intelligence model that is trained according to the machine learning algorithm. A type of the artificial intelligence model is not limited thereto and other general types of artificial intelligence models trained according to the machine learning algorithm may be applied.

Here, the learning data is described as including biodata at the time when each of the plurality of traders transmits a transaction request, a transaction signal output according to the transaction request of each of the plurality of traders, and a rate of return according to the output transaction signal but is not limited thereto. Therefore, the learning data may further include transaction history data including at least one of the trader's past financial product transaction data, rate of return data, and trader's personal information data, test result data about tests conducted on the trader before the opening of the financial product market, and financial data including at least one of technical indicators, financial statements, performances, news, and chart patterns.

The first artificial intelligence model (or a computational model, a nerve network, a network function, or a neural network) is configured by one or more network functions. One or more network functions are configured by a set of interconnected computational units that are generally referred to as "nodes". The "nodes" may also be referred to as "neurons". One or more network functions includes at least one or more nodes. The nodes (or neurons) that configure one or more network functions may be connected to each other by one or more "links".

In the first artificial intelligence model, one or more nodes connected through the link may relatively form a relation of an input node and an output node. Concepts of the input node and the output node are relative so that an arbitrary node that serves as an output node for one node may also serve as an input node for the other node and vice versa. As described above, an input node to output node relationship may be created with respect to the link. One or more output nodes may be connected to one input node through the link and vice versa.

In the input node and output node relationship connected through one link, a value of the output node may be determined based on data input to the input node. The node connecting the input node and the output node to each other may have a weight. The weight may be variable and may vary by the user or the algorithm to allow the first artificial intelligence model to perform a desired function. For example, when one or more input nodes are connected to one output node by each link, the output node may determine an output node value based on values input to the input nodes connected to the output node and a weight set to the link corresponding to the input nodes.

As described above, in the first artificial intelligence model, one or more nodes are interconnected through one or more links to form an input node and output node relationship in the first artificial intelligence model. In the first artificial intelligence model, a characteristic of the first artificial intelligence model may be determined in accordance with the number of the nodes and links and a correlation between the nodes and links, and a weight assigned to each link. For example, when there are two first artificial intelligence models in that the same number of nodes and links are provided and weights value between links are different, the two first artificial intelligence models may be recognized to be different from each other.

Some of the nodes that configure the first artificial intel-ligence model may configure one layer based on distances from an initial input node. For example, a set of nodes with a distance n from the initial input node may configure n layers. The distance from the initially input node may be defined by a minimum number of links that need to go through to reach from the initial input node to the corre-sponding node. However, the definition of the layer is arbitrary provided for description and the dimensionality of the layer in the first artificial intelligence model may be defined differently from the above description. For example, the layer of the nodes may be defined by a distance from the final output node.

The initial input node may refer to one or more nodes to that data is directly input without passing through the link in the relationship with other nodes, among the nodes in the first artificial intelligence model. Alternatively, in the first artificial intelligence model network, in the relationship between nodes with respect to the link, the initial input node may refer to nodes that do not have other input nodes linked by the link. Similarly, the final output node may refer to one or more nodes that do not have an output node, in the relationship with other nodes, among the nodes in the first artificial intelligence model. Further, a hidden node may refer to nodes that configure the first artificial intelligence model, rather than the initial input node and the finally output node. In the first artificial intelligence model accord-ing to one embodiment of the present invention, nodes of the input layer may be more than nodes of the hidden layer close to the output layer and the number of nodes is reduced as it progresses from the input layer to the hidden layer.

The first artificial intelligence model may include one or more hidden layers. A hidden node of the hidden layer may have an output of a previous layer and an output of a surrounding hidden node as inputs. The number of hidden nodes for every hidden layer may be equal or different. The number of nodes of the input layer is determined based on the number of data fields of the input data and may be equal to or different from the number of hidden nodes. The input data input to the input layer is computed by the hidden node of the hidden layer and is output by a fully connected layer (FCL) that is an output layer.

In various embodiments, the computing device 100 may construct learning data to train the first artificial intelligence model and train the first artificial intelligence model by at least one of supervised learning, unsupervised learning, and semi supervised learning using the constructed learning data.

The training of the first artificial intelligence model is to minimize an error of the output. This is a process of updating a weight of each node of the first artificial intelligence model by repeatedly inputting the learning data to the first artificial intelligence model, calculating an error of an output and a target of the first artificial intelligence model for the learning data, and back-propagating an error of the first artificial intelligence model from the output layer of the first artificial intelligence model to the input layer aimed at reducing the error during the training of the first artificial intelligence model.

In the case of the supervised learning, learning data (that is, labeled learning data) labeled with a correct answer is used for each learning data, but in the case of the unsuper-vised learning, the correct answer may not be labeled to each learning data. That is, for example, the learning data of the supervised learning for data classification may be learning data labeled with category. The labeled learning data is input to the first artificial intelligence model and the error may be calculated by comparing the output (category) of the first artificial intelligence model and the label of the learning data.

As another example, in the case of the unsupervised learning for data classification, an error may be calculated by comparing the learning data that is an input with the first artificial intelligence model output. The calculated error is back-propagated in a reverse direction (that is, a direction from the output layer to the input layer) in the first artificial intelligence model and a connection weight of each node of each layer of the first artificial intelligence model may be updated in accordance with the backpropagation. A variation of the connection weight of the nodes to be updated may vary depending on a learning rate.

The calculation of the first artificial intelligence model for the input data and the backpropagation of the error may construct a learning epoch. The learning rate may be differ-ently applied depending on the repetitive number of the learning epochs of the first artificial intelligence model. For example, at the beginning of the training of the first artificial intelligence model, the first artificial intelligence model quickly ensures a predetermined level of performance using a high learning rate to increase efficiency and at the late stage of the learning, the low learning rate is used to increase the accuracy.

In the training of the first artificial intelligence model, normally, the learning data may be a sub set of the actual data (that is, data to be processed using the trained first artificial intelligence model). Therefore, there may be a learning cycle that the error of the learning data is reduced, and the error is increased for the actual data. The overfitting is a phenomenon in that the learning data is excessively learned so that an error for real data is increased. For example, a phenomenon that a first artificial intelligence model that learns a cat by watching a yellow cat does not recognize a cat other than the yellow cat as a cat may be a sort of overfitting.

The overfitting may act as a cause of the increase of the error of the machine learning algorithm. In order to prevent the overfitting, various optimization methods may be used. In order to prevent the overfitting, a method of increasing training data, regularization, or dropout that omits some nodes of the network during the learning process may be applied.

In various embodiments, when a transaction request for a financial product is acquired from one trader, the computing device 100 inputs biodata about the trader that is collected for a predetermined period from a time when the transaction request for the financial product is acquired to the first artificial intelligence model to extract result data for the processing mode for the acquired transaction request. For example, as illustrated in FIG. 4, when the transaction request for a financial product is acquired from one trader, the computing device 100 inputs a one-dimensional vector that is biodata about the trader at a time when the transaction request for the financial product is acquired to the first artificial intelligence model to extract result data about the processing mode for the acquired transaction request.

In various embodiments, when transaction requests for a financial product are acquired from a plurality of traders (for example, simultaneously or within a predetermined period), the computing device 100 inputs biodata about the plurality of traders that is collected for a predetermined period from a time when the transaction requests for the financial product are acquired to the first artificial intelligence model to extract result data for the processing mode for the transac-tion requests acquired from the plurality of traders. For example, as illustrated in FIG. 5, when transaction requests for a financial product are acquired from the plurality of traders, the computing device 100 may determine a processing mode for collectively processing the transaction requests obtained from the plurality of traders by generating a plurality of multi-dimensional matrix data (for example, a plurality of one-dimensional vectors or a multi-dimensional matrix that is biodata at a plurality of times is combined to generate multi-dimensional matrix data that is biodata for a predetermined period) using biodata collected from each of the plurality of traders, and generating one multi-dimensional matrix data by combining a plurality of generated multi-dimensional matrix data, and inputting the generated one multi-dimensional matrix data to the first artificial intelligence model.

Here, the processing mode determined for the transaction requests acquired from the plurality of traders may be individually determined for each of the plurality of traders according to the result data of the first artificial intelligence model, but is not limited thereto. The processing mode may be integrally determined for the plurality of traders to collectively apply the processing mode for the transaction request for a specific financial product, that is, the same financial product.

In various embodiments, the computing device 100 inputs biodata for the trader that is collected for the past N minutes, as of a time when the transaction request for the financial product is acquired to the first artificial intelligence model to extract result data for the processing mode for the acquired transaction request. For example, the computing device 100 collects biodata about the trader at every predetermined unit time for the past N minutes (for example, 10 minutes) as of a time when the transaction request for the financial product is acquired, combines a plurality of one-dimensional vectors that is the plurality of collected biodata to generate two-dimensional biodata. The computing device 100 inputs the two-dimensional biodata to the first artificial intelligence model to extract result data about the processing mode for the acquired transaction request.

In various embodiments, when the transaction request for the financial product is acquired from the trader, the computing device 100 inputs biodata about the trader that is collected at every predetermined unit time from the opening (for example, if the financial product is a stock, 9 a.m. is the regular opening of the stock market) of the transaction market of the financial product to the time when the transaction request is acquired, to the first artificial intelligence model to extract result data about the processing mode for the acquired transaction request.

In various embodiments, the computing device 100 inputs the biodata about the trader for a predetermined period in the past as of the time when the transaction request for the financial product is acquired (for example, for the past N minutes as of the time when the transaction request is acquired or from the opening of the transaction market of the financial product to the time when the transaction request is acquired) to the previously trained artificial intelligence model to extract result data about the trader's state at the time when the transaction request for the financial product is acquired. The computing device 100 may extract the result data about the processing mode for the transaction request acquired from the trader using the extracted result data about the trader's state.

For example, the computing device 100 inputs the biodata of the specific trader to the previously trained artificial intelligence model (for example, second artificial intelligence model) to extract result data about a state of the specific trader. The computing device 100 may determine the processing mode according to the trader's state using the state of the specific trader and processing mode data for every state that has been stored in advance.

Here, the second artificial intelligence model is a model that is trained with biodata according to a state of each of the plurality of traders as learning data (for example, trained according to supervised learning method with biodata labeled with the trader's state as learning data) and may be a model that receives the biodata of the trader as input data to extract result data about the trader's state, but is not limited thereto.

Here, the trader's state may include not only physical and mental state (emotion) of the trader, but also the trader's cognitive state. For example, the trader's state may include at least one of perception, learning, memory, attention, motivation, valence, arousal, happiness, fear, relaxation, excitement, introvert/extrovert personality, and stress, but is not limited thereto.

Here, it is described that the computing device 100 trains the second artificial intelligence model, that is independently constructed from the previously trained first artificial intelligence model, with biodata according to the state of each of the plurality of traders as learning data to determine the trader's state using the second artificial intelligence model. However, it is not limited thereto and in order to determine the trader's state, the first artificial intelligence model is trained with biodata according to the state of each of the plurality of traders as learning data to perform all the above-mentioned operations using only one artificial intelligence model.

In various embodiments, the computing device 100 may determine a processing mode for the transaction request using the trader's state determined from the biodata of the trader and a predetermined reference value. For example, the computing device 100 inputs the biodata about the trader during the predetermined period in the past as of the time when the transaction request for the financial product is acquired, to the previously trained artificial intelligence model to calculate a stress index for the trader.

Thereafter, when the stress index calculated according to the above-described method exceeds a first reference value (when it is determined that the trader's state is abnormal), the computing device 100 may determine to stand by or oppose the processing mode for the transaction request obtained from the trader (for example, selling for the buying request or buying for the selling request).

In the meantime, when the stress index calculated according to the above-described method is equal to or lower than the first reference value (when it is determined that the trader's state is normal), the computing device 100 may determine to process the processing mode for the transaction request obtained from the trader according to the transaction request obtained from the trader.

In various embodiments, data about the trader further includes transaction history data and test result data. The computing device 100 inputs at least one of the transaction history data and the test result data to the artificial intelligence model together with the biodata to determine the processing mode for the transaction request.

Here, the transaction history data includes at least one data of the trader's past financial product transaction data, rate of return data, and trader's personal information data, but is not limited thereto.

Further, the test result data may include result data about tests conducted on the trader before the opening of the financial product market. Here, the tests conducted on the trader may be meditation, concentration, and motivation tests, but are not limited thereto. Further, a method for conducting a test on the trader is not limited to one method, but various methods such as text type survey tests or image type tests may be applied.

In various embodiments, the computing device 100 may collect financial data (for example, including at least one of technical indicators, financial statements, performance, news, and chart patterns) from the external server 300. The computing device 100 may input the collected financial data to the artificial intelligence model together with the biodata about the trader to determine the processing mode for the transaction request.

That is, the computing device 100 uses a total of four data of biodata, transaction history data, test result data, and financial data and in this case, the biodata is used as a default. And at least one data of the remaining data of the transaction history data, the test result data, and the financial data is flexibly used together to determine the processing mode for the transaction request.

For example, the computing device 100 may determine the processing mode using only the biodata. Or, the computing device 100 may determines the processing mode for the transaction request using any one data of the transaction history data, the test result data, and the financial data and the biodata. Or, the computing device 100 may determine the processing mode for the transaction request using two of the biodata, the transaction history data, the test result data, and the financial data and the biodata. Or, the computing device 100 may determine the processing mode for the transaction request using all four data.

Here, the computing device 100 uses the biodata about the trader as a default. When additional data is acquired in addition to the biodata, the computing device 100 uses the additionally acquired data as the input of the artificial intelligence model together with the biodata to determine the processing mode. Here, even though it is described that at least one data of the transaction history data, the test result data, and the financial data and the biodata are used together to determine the processing mode, in order to more accurately determine the processing mode, all collectable data is desirably used together as input data to determine the processing mode.

In various embodiments, the computing device 100 determines the processing mode using the biodata. In that case, the computing device 100 may be implemented to extract a result with a higher reliability by individually determining the processing mode for the transaction request with each of the transaction history data, the test result data, and the financial data as an input of the previously trained artificial intelligence model. the computing device 100 may verify the processing mode determined using the biodata based on the processing mode determined using the transaction history data, the processing mode determined using the test result data, and the processing mode determined using the financial data.

In various embodiments, the computing device 100 may calculate an expected rate of return of the trader using at least one data of the biodata, the transaction history data, the test result data, and the financial data. The computing device 100 may correct the determined processing mode for the transaction request based on the calculated expected rate of return.

Further, the computing device 100 may calculate a probability of price increase of the financial product using biodata that is collected from the plurality of traders for a predetermined period from the time when information about the financial product is provided to the plurality of traders. The computing device 100 may correct the determined processing mode for the transaction request based on the calculated probability of price increase of the financial product. Hereinafter, a processing mode correcting method performed by the computing device 100 will be described with reference to FIGS. 6 to 8.

Figure 7:
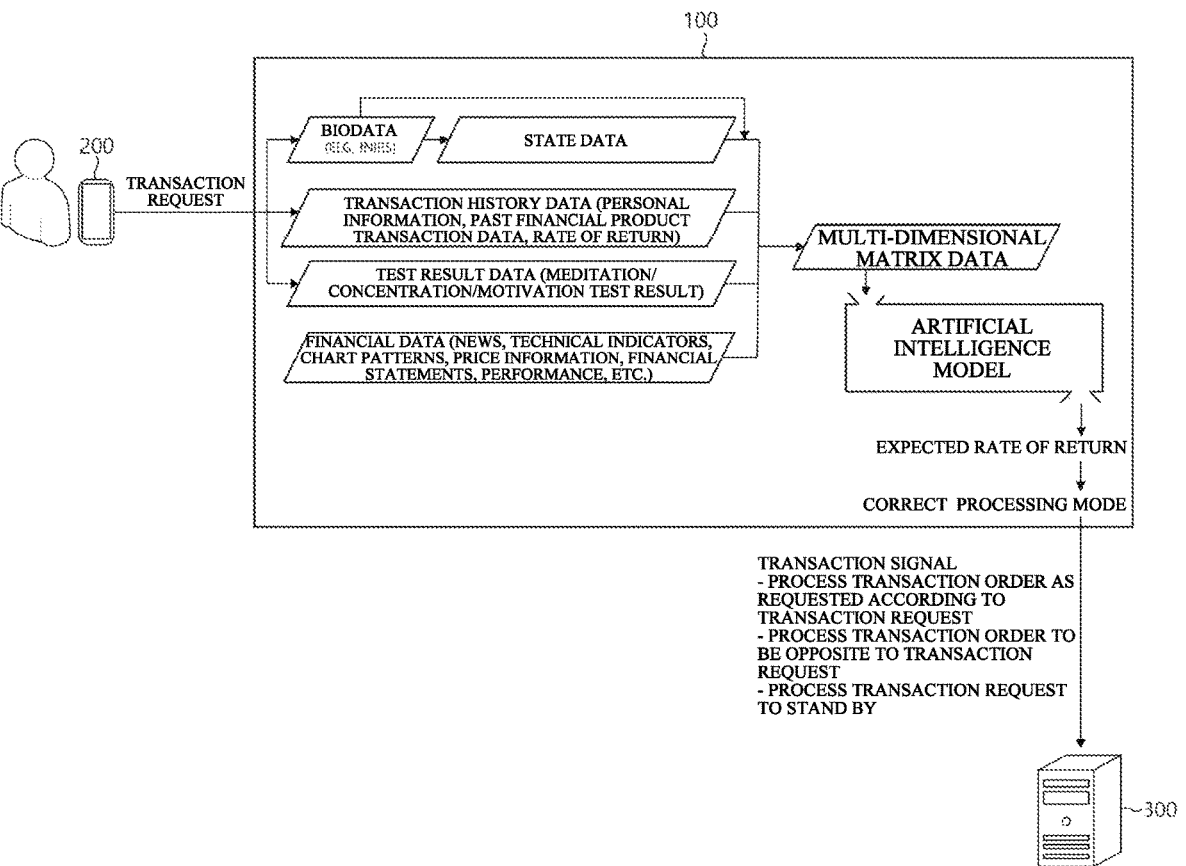
FIG. 7 is a view illustrating a process of performing a method for correcting a processing mode for a transaction request based on an expected rate of return of a trader, in various exemplary embodiments.

FIG. 6 is a flowchart for explaining a method for correcting a processing mode for a transaction request based on an expected rate of return of a trader, in various exemplary embodiments and FIG. 7 is a view illustrating a process of performing a method for correcting a processing mode for a transaction request based on an expected rate of return of a trader, in various exemplary embodiments.

Here, it is described that the method for correcting a processing mode for a transaction request of FIGS. 6 and 7 is performed by a computing device 100, but is not limited thereto and is independently performed in a trader terminal 200 as the trader terminal 200 executes software provided from the computing device 100.

Referring to FIGS. 6 and 7, in step S210, the computing device 100 may calculate an expected rate of return of a specific trader using at least one data of biodata, transaction history data, test result data, and financial data of the specific trader.

Here, the expected rate of return of the trader may refer to a probability that the trader will close with a profit (or probability of closing with a loss) on the date that includes the time of calculating the expected rate of return of the trader, but is not limited thereto.

In various embodiments, the computing device 100 inputs at least one of the biodata, the transaction history data, the test result data, and the financial data of the specific trader as input data, to the previously trained artificial intelligence model (for example, the third artificial intelligence model) to extract result data about the expected rate of return of the trader. For example, the computing device 100 inputs a one-dimensional vector that is the biodata of the trader to the third artificial intelligence model at the time when the transaction request for the financial product is acquired, to extract the expected rate of return of the trader.

Here, the third artificial intelligence model may be a model trained with the biodata, the transaction history data, the test result data, the financial data, and the rate of return of the trader as learning data. Further, here, the third artificial intelligence model is implemented to be the same as or similar to the first artificial intelligence model or implemented to calculate an expected rate of return of a specific trader, through the first artificial intelligence model, but is not limited thereto.

In step S220, the computing device 100 may correct the processing mode determined for the transaction request of the trader, based on the expected rate of return of the trader calculated in step S210.

In various embodiments, the computing device 100 may correct the processing mode to adjust a fund and a transaction size allocated to the trader in proportion to the expected rate of return calculated in step S210 (for example, corrects to reduce the fund and the transaction size allocated to the trader as the expected rate of return is smaller).

In various embodiments, the computing device 100 may change the processing mode for the transaction request, based on the expected rate of return calculated in step S210. For example, when the calculated expected rate of return is lower than a first reference value (for example, 0.35), the computing device 100 may change the processing mode determined for the specific trader to be opposite (for example, buying is changed to selling and selling is changed to buying). When the calculated expected rate of return is in the range equal to or higher than the first reference value and lower than a second reference value (for example, 0.65), the computing device may change the transaction request for the specific trader to be a stand-by state and when the calculated expected rate of return is equal to or higher than the second reference value, the computing device may maintain the transaction request determined for the specific trader as it is.

Thereafter, the computing device 100 may construct the learning data based on the transaction request for a specific trader, the processing mode (or a corrected processing mode) determined for the transaction request, and the rate of return of the specific trader. The computing device 100 may train the first artificial intelligence model again using the constructed learning data to consistently improve a result data extraction performance of the first artificial intelligence model.

Here, the computing device 100 is described to correct the previously determined processing mode for the transaction request based on an expected profit rate of the trader calculated by analyzing data about the trader, but is not limited thereto. If necessary, the computing device 100 may determine the processing mode for the transaction request acquired from the trader using only the expected profit rate of the trader.

For example, when the transaction request acquired from the trader is a buying request for a specific financial product, the computing device 100 may determine the processing mode to process the buying request of the trader to be opposite (to sell) if the predicted profit rate of the trader calculated by the above method is lower than the first reference value (0.35), determine the processing mode to process the buying request of the trader on hold if the profit rate of the trader is equal to or higher than the first reference value and lower than a second reference value (0.65), and determine the processing mode to normally process the buying request of the trader (to buy) if the expected profit rate of the trader is equal to or higher than the second reference value.

Figure 8:
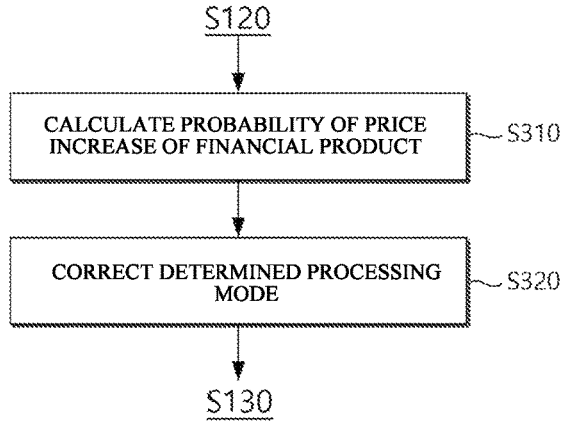
FIG. 8 is a flowchart for explaining a method for correcting a processing mode for a transaction request based on a probability of price increase of a financial product, in various exemplary embodiments.

FIG. 8 is a flowchart for explaining a method for correcting a processing mode for a transaction request based on a probability of price increase of a financial product, in various exemplary embodiments.

Here, it is described that the method for correcting a processing mode for a transaction request of FIG. 8 is performed by the computing device 100, but is not limited thereto and may be independently performed in a trader terminal 200 as the trader terminal 200 executes software provided from the computing device 100.

Referring to FIG. 8, in step S310, the computing device 100 may provide information about a financial product to a plurality of traders. the computing device 100 may calculate a probability of price increase of the financial product using biodata that is collected from the plurality of traders for a predetermined period from the time when information about the financial product is provided to the plurality of traders. For example, the computing device 100 inputs the biodata that is collected from the plurality of traders for a predetermined period from the time when information about the financial product is provided to the plurality of traders to the previously trained artificial intelligence model (for example, a fourth artificial intelligence model) as input data to calculate the probability of price increase for the financial product. Here, a more specific method for calculating the probability of price increase of the financial product using the fourth artificial intelligence model will be described below with reference to FIG. 9.

In step S320, the computing device 100 may correct the processing mode for the transaction request based on the probability of price increase of the financial product calculated in step S320. For example, when a buying request for a first financial product is input from the specific trader and the buying request for the first financial product is normally processed according to the method (for example, S120) to determine to output a buying signal, but the probability of price increase of the first financial product calculated in step S310 is lower than the predetermined first reference value (for example, 0.35), the processing mode may be corrected to change the buying request for the first financial product to a selling request. Further, when a selling request for the first financial product is normally processed according to the method (for example S120) to determine to output a selling signal, but the probability of price increase of the first financial product calculated in step S310 is equal to or higher than a predetermined second reference value (for example, 0.65), the processing mode may be corrected to hold the selling request for the first financial product or change the selling request to a buying request.

Referring to FIG. 3 again, in step S130, the computing device 100 may output a transaction signal corresponding to the processing mode determined by an operation (for example, step S120) of determining the processing mode for the transaction request. For example, when the buying request for the specific financial product is received from the trader and the processing mode for the buying request received from the trader is determined to be processed according to the buying request acquired from the trader based on biodata (or, at least one of transaction history data, test result data, and financial data is additionally considered) of the corresponding trader, the computing device 100 may output a buying signal to buy a specific financial product according to the request received from the trader.

In the meantime, when the buying request for the specific financial product is received from the trader, but the processing mode for the buying request received from the trader is determined to be processed to be opposite to the buying request acquired from the trader based on biodata (or, at least one of transaction history data, test result data, and financial data is additionally considered) of the corresponding trader, the computing device 100 outputs a selling signal to sell a specific financial product based on the request received from the trader.

In various embodiments, when the computing device 100 acquires a buying or selling request for a specific financial product from the trader, but the result of determining the processing mode for the request is opposite to the request from the trader, the computing device 100 processes the transaction request (buying or selling request) acquired from the trader to stand by or may ignore the transaction request (invalidates the transaction request acquired from the trader).

In various embodiments, when the processing mode for the transaction request acquired from the trader is not determined due to a system error or an operation of determining the processing mode is delayed due to a large amount of data to be processed so that the operation of determining the processing mode is not performed, the computing device 100 may process the transaction request to stand by.

Here, the computing device 100 may output the transaction signal to a securities company server or a HTS server that processes the buying or transaction of the financial product, but is not limited thereto. When the computing device 100 may independently buy or trade the financial product, that is, when the computing device 100 is integrally coupled to the securities company server or the HTS server, the computing device may proceed the buying or transaction according to the processing mode determined for the transaction request without a separate operation of outputting a transaction signal. Hereinafter, a financial product transaction method using an artificial intelligence model according to a second embodiment will be described with reference to FIGS. 9 to 12.

Figure 9:
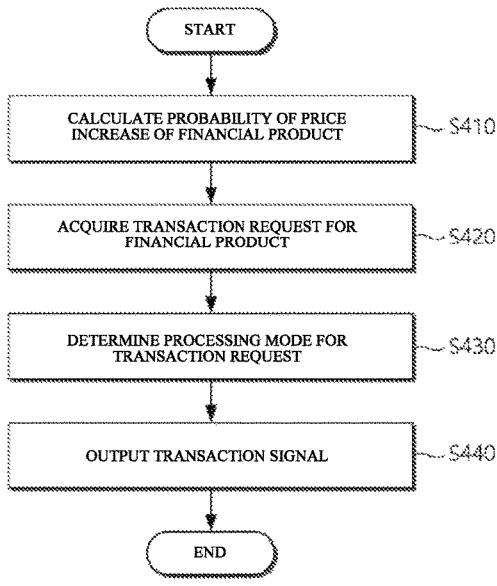
FIG. 9 is a flowchart for explaining a second embodiment of a financial product transaction method using an artificial intelligence model according to still another exemplary embodiment of the present invention.
Figure 10:
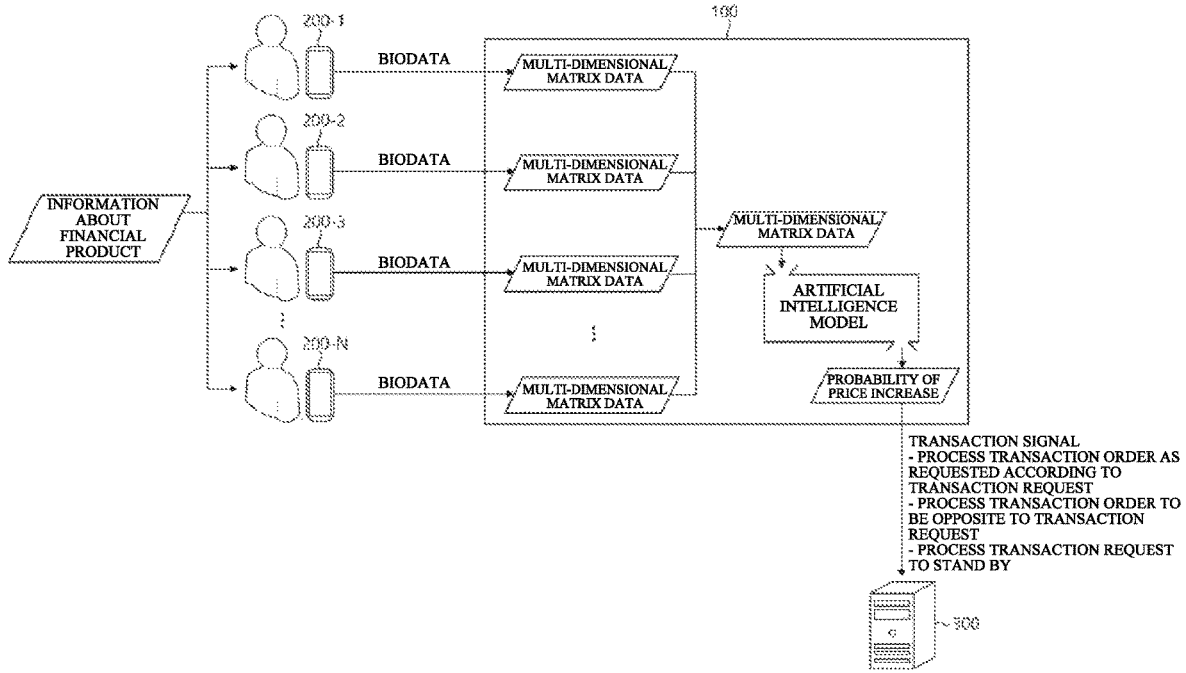
FIG. 10 is a view illustrating a process of performing a financial product transaction method according to a second embodiment, in various exemplary embodiments.

FIG. 9 is a flowchart for explaining a second embodiment of a financial product transaction method using an artificial intelligence model according to still another exemplary embodiment of the present invention and FIG. 10 is a view illustrating a process of performing a financial product transaction method according to a second embodiment, in various exemplary embodiments.

Here, it is described that a financial product transaction method using an artificial intelligence model of FIGS. 9 and 10 is performed by a computing device 100, but is not limited thereto and may be independently performed in a trader terminal 200 as the trader terminal 200 executes software provided from the computing device 100.

Referring to FIGS. 9 and 10, in step S410, the computing device 100 may calculate a probability of price increase for a plurality of financial products.

First, the computing device 100 may be connected to trader terminals 200 of the plurality of traders through the network 400 and provide information about a financial product to the trader terminals 200.

Here, the information about the financial product is information about a price index of stocks, stocks, and bonds and may include charts of financial products, price fluctuations, and news texts, but is not limited thereto.

In various embodiments, the computing device 100 may collectively provide information about the financial products to the plurality of traders before a predetermined time in the past (for example, approximately 2 minutes) as of a previously determined transaction time. For example, when the transaction time is set to 10 minutes after the opening of the financial product trading floor, the computing device 100 may provide information about the financial products to the plurality of traders about 2 minutes before the transaction time, that is, 8 minutes after the opening of the financial product trading floor.

At this time, the computing device 100 calculates a probability of price increase of the financial product using data (for example, bio data) collected while the plurality of traders checks the information about the financial product so that it is necessary to ensure that the plurality of traders checks the information about the financial product provided from the computing device 100. In consideration of this, the computing device 100 sets performing of the operation of checking the information about the financial products provided by the computing device 100 as a requirement for using the financial product transaction service using the artificial intelligence model provided by the computing device 100 to induce the plurality of traders to read the information about the financial products.

Thereafter, the computing device 100 may collect biodata from the plurality of traders for a predetermined time (10 minutes after the opening of the financial product trading floor, that is, for about 2 minutes) from the time when the information about the financial products is provided to the plurality of traders (8 minutes after the opening of the financial product trading floor). Here, the biodata collecting method performed by the computing device 100 may be implemented to be the same as or similar to the biodata collecting method performed in step S120 of FIG. 3, but is not limited thereto.

Thereafter, the computing device 100 may generate multi-dimensional matrix data using the biodata collected from the plurality of traders. For example, when the biodata collected from the plurality of traders is EGG data and the EEG data for each of the plurality of traders is collected from an EEG device including eight channels N times per second, [8 channels×(120*N) times] matrix data for every trader may be generated. The matrix data for each of the plurality of traders (for example, M traders) is coupled to generate ([8 channels×(120*N) times×M] (here, when EEG data is collected twice per second for 100 traders, 8×240×100) three-dimensional matrix data (tensor).

Thereafter, the computing device 100 inputs the multi-dimensional matrix data generated according to the above-described method to the fourth artificial intelligence model as input data to extract result data about a probability of price increase of financial products.

Here, the previously trained fourth artificial intelligence model may be a model that is trained with information about the plurality of financial products, a plurality of biodata collected from the plurality of traders at the time when the information about the plurality of financial products is provided, a plurality of multi-dimensional matrix data generated using the plurality of biodata, and price changes of the plurality of financial products as learning data. Further, the fourth artificial intelligence model may be implemented to be the same as or similar to the first artificial intelligence model, but is not limited thereto.

In step S420, the computing device 100 may acquire transaction requests for the financial products from the plurality of traders. Here, the transaction request acquiring method performed by the computing device 100 may be implemented to be the same as or similar to the transaction request acquiring method performed in step S110 of FIG. 3, but is not limited thereto.

In step S430, the computing device 100 may determine a processing mode for the transaction request of the financial product acquired in step S420 based on the probability of price increase of the financial product calculated in step S410. For example, when the transaction request acquired in step S420 is a buying request for a specific financial product, the computing device 100 may determine the processing mode to normally process the buying request of the trader if the probability of price increase of the specific financial product calculated in step S410 is equal to or higher than the predetermined second reference value (for example, 0.65). For example, the computing device 100 may determine the processing mode to reversely process the buying request of the trader (for example, to sell the specific financial product) if the probability of price increase is lower than the predetermined first reference value (for example, 0.35). Further, if the probability of price increase is in the range that is equal to or higher than the first reference value and lower than the second reference value, the computing device 100 may determine the processing mode to process the buying request acquired from the trader on hold (for example, to make the buying request stand by so as not to be processed).

Further, when the transaction request acquired in step S420 is a selling request for a specific financial product, the computing device 100 may determine the processing mode to reversely process the selling request of the trader if the probability of price increase of the specific financial product calculated in step S410 is equal to or higher than the predetermined second reference value (for example, 0.65).

For example, the computing device 100 may determine the processing mode to normally process the selling request of the trader (for example, to sell the specific financial product according to the selling request) if the probability of price increase is lower than the predetermined first reference value (for example, 0.35). Further, if the probability of price increase is in the range that is equal to or higher than the first reference value and lower than the second reference value, the computing device 100 may determine the processing mode to process the selling request acquired from the trader (for example, to make the selling request stand by so as not to be processed) to be held.

In various embodiments, the computing device 100 may correct the processing mode for the transaction request using the biodata of the trader for a predetermined period in the past as of the time when the transaction request for the financial product is acquired from the trader.

For example, the computing device 100 may correct the processing mode for the transaction request of a specific trader, based on an expected rate of return of the specific trader.

To be more specific, the computing device 100 may calculate an expected rate of return of the specific trader using biodata collected for a predetermined period in the past (for example, for past N minutes (for example, 10 minutes) as of the time when the transaction request is acquired or a time when the transaction request is acquired from the opening of the trading market of the financial product), as of the time when the transaction request for a financial product is acquired from the specific trader. Here, the expected rate of return calculating method of the specific trader may be implemented to be the same as or similar to the expected rate of return calculating method in step S210 of FIG. 5.

Thereafter, the computing device 100 may correct the processing mode determined for the transaction request of the trader, based on the calculated expected rate of return. For example, the computing device 100 may correct the processing method to adjust a fund and a transaction size allocated to the trader in proportion to the expected rate of return of the trader (for example, corrects to adjust such that the smaller the expected rate of return, the smaller the fund and the transaction size allocated to the trader), but is not limited thereto.

As another example, the computing device 100 may correct the processing mode for the transaction request based on the state of the trader.

To be more specific, the computing device 100 may determine the state of the trader using biodata collected for a predetermined period in the past (for example, for past N minutes (for example, 10 minutes) as of the time when the transaction request is acquired or a time when the transaction request is acquired from the opening of the trading market of the financial product), as of the time when the transaction request for a financial product is acquired from the specific trader. Here, the method for determining the trader's state may be implemented to be the same as or similar to the method for determining the trader's state in step S120 of FIG. 3.

Thereafter, the computing device 100 may determine an attribute (for example, negative or positive) of the state of the trader using processing mode data for every state that has been stored in advance and may correct the processing mode according to the determined attribute. For example, when the processing mode determined for the buying request acquired from the trader is outputting of a buying signal or the trader's state determined by analyzing the biodata of the trader corresponds to a predetermined negative state, the computing device 100 may correct the outputting of the buying signal that is the previously determined processing mode to holding or outputting of a selling signal.

In various embodiments, the computing device 100 may correct the processing mode for the transaction request based on occurrence of an event for the financial product, and this will be described below with reference to FIGS. 11 and 12.

Figure 11:
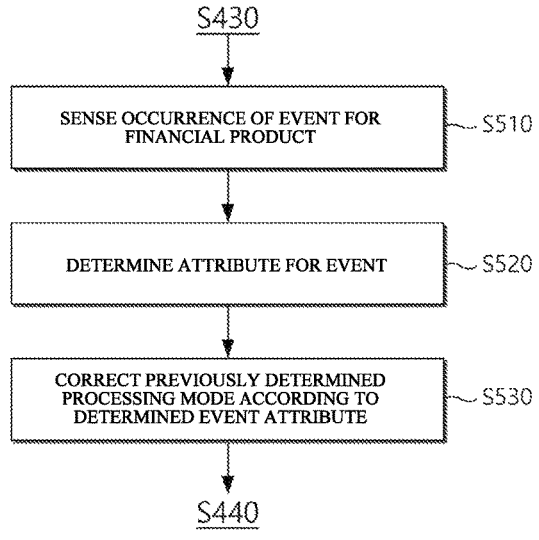
FIG. 11 is a flowchart of a method for correcting a processing mode for a transaction request based on event occurrence of a financial product, in various exemplary embodiments.
Figure 12:
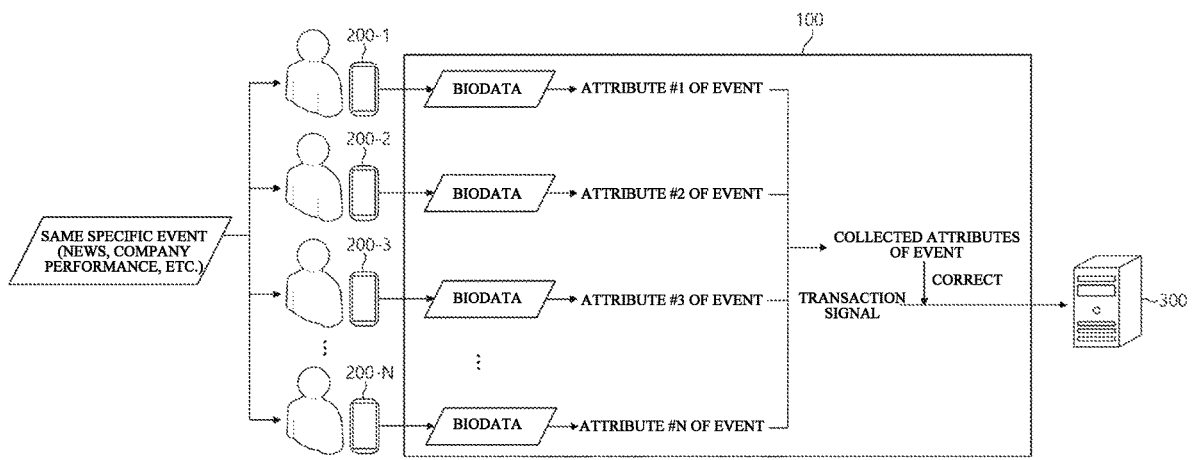
FIG. 12 is a view illustrating a process of performing a method for correcting a processing mode for a transaction request based on event occurrence of a financial product, in various exemplary embodiments.

FIG. 11 is a flowchart of a method for correcting a processing mode for a transaction request based on event occurrence of a financial product, in various exemplary embodiments and FIG. 12 is a view illustrating a process of performing a method for correcting a processing mode for a transaction request based on event occurrence of a financial product, in various exemplary embodiments.

Here, it is described that the method for correcting a processing mode for a transaction request of FIGS. 11 and 12 is performed by a computing device 100, but is not limited thereto and is independently performed in a trader terminal 200 as the trader terminal 200 executes software provided from the computing device 100.

Referring to FIGS. 11 and 12, in step S510, the computing device 100 may detect event occurrence for a specific financial product.

In various embodiments, the computing device 100 may collect data (for example, news data, company performance announcement data, or SNS data) about a plurality of financial products from the external server 300, may extract one or more keywords from the collected data about the plurality of financial products, and analyzes one or more extracted keywords to detect the event occurrence for the financial product.

For example, the computing device 100 may collects text type news data and company performance announcement data and analyzes the collected data using an optical character reader (OCR) to extract one or more keywords and matches the extracted one or more keywords and the previously stored keyword for every event to detect the event occurrence for the financial product, but is not limited thereto.

In step S520, the computing device 100 may determine an attribute of the event for the financial product detected in step S510, using biodata for the plurality of traders.

First, the computing device 100 may provide information of the event for the financial product detected in step S510 to the plurality of traders. For example, the computing device 100 is connected to the trader terminals 200 for the plurality of traders through the network 400 to provide UI to the trader terminals 200. The computing device 100 may provide information about the event for the financial product through the UI, but is not limited thereto.

Thereafter, the computing device 100 may collect biodata from the plurality of traders for a predetermined period from the time when the information about the event is provided to the plurality of traders. Here, the biodata collecting method performed by the computing device 100 is implemented to be the same as or similar to the biodata collecting method performed in step S120 of FIG. 3, but is not limited thereto.

Thereafter, the computing device 100 inputs the biodata of the plurality of traders to the previously trained artificial intelligence model to extract result data about the attribute (for example, positive or negative) of the event.

In various embodiments, the computing device 100 inputs the biodata of the plurality of traders to the second artificial intelligence model to extract state information about the biodata of the plurality of traders. The computing device 100 may determine the attribute of the event based on the attribute of the extracted state information (for example, determines the attribute of the event by calculating the difference of the number of state information having a negative attribute and the number of state information having a positive attribute, among the plurality of state information), but is not limited thereto.

In step S530, the computing device 100 may correct the determined processing mode based on the attribute for the event determined in step S520.

For example, when the computing device 100 determines to sell the specific financial product in response to the transaction request of the plurality of traders, but the event occurrence for the specific financial product is detected and the occurring event has a positive attribute, that is, favorable news occurs for the specific financial product, the computing device 100 may wait without selling the specific financial product or changes the processing mode to buy.

Here, when the computing device 100 determines to sell the specific financial product in response to the transaction request of the plurality of traders, but the event having a negative attribute for the specific financial product occurs, that is, bad news occurs, the computing device 100 may increase the selling quantity for the specific financial product.

Further, when the computing device 100 determines to buy the specific financial product in response to the transaction request of the plurality of traders, but the event occurrence for the specific financial product is detected and the occurring event has a negative attribute, that is, bad news occurs for the specific financial product, the computing device 100 may wait without buying the specific financial product or changes the processing mode to sell.

Here, when the computing device 100 determines to buy the specific financial product in response to the transaction request of the plurality of traders, but the event having a positive attribute for the specific financial product occurs, that is, favorable news occurs, the computing device 100 may increase the buying quantity for the specific financial product, but is not limited thereto.

Referring to FIG. 9 again, in step S440, the computing device 100 may output a transaction signal corresponding to the processing mode determined by an operation (for example, step S430) of determining the processing mode for the transaction request. For example, when the processing mode for the buying request received from the trader is determined to be processed in accordance with the buying request acquired from the trader based on the probability of price increase for the financial product, the computing device 100 may output a buying signal to buy the specific financial product in accordance with the request received from the trader.

In the meantime, when a buying request for the specific financial product is received from the trader, but the processing mode for the buying request received from the trader is determined to be processed to be opposite to the buying request acquired from the trader based on the probability of price increase for the financial product, the computing device 100 may output a selling signal to sell the specific financial product based on the request received from the trader.

In various embodiments, when the computing device 100 acquires a buying or selling request for a specific financial product from the trader, but the result of determining the processing mode for the request is opposite to the request from the trader, the computing device 100 processes the transaction request (buying or selling request) acquired from the trader to stand by or may ignore the transaction request (invalidate the transaction request acquired from the trader).

In various embodiments, when the processing mode for the transaction request acquired from the trader is not determined due to a system error or an operation of determining the processing mode is delayed due to a large amount of data to be processed so that the operation of determining the processing mode is not performed, the computing device 100 may process the transaction request to stand by. Hereinafter, a financial product transaction method using an artificial intelligence model according to a third embodiment will be described with reference to FIGS. 13 and 14.

Figure 13:
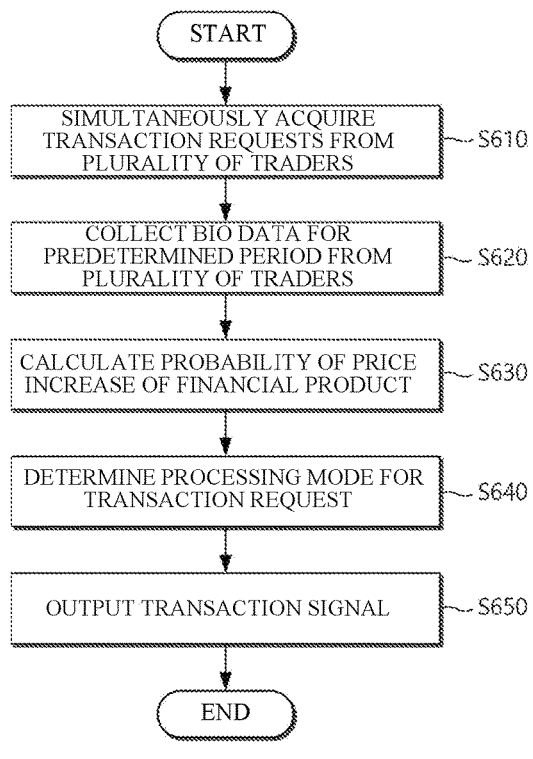
FIG. 13 is a flowchart for explaining a third embodiment of a financial product transaction method using an artificial intelligence model according to still another exemplary embodiment of the present invention.
Figure 14:
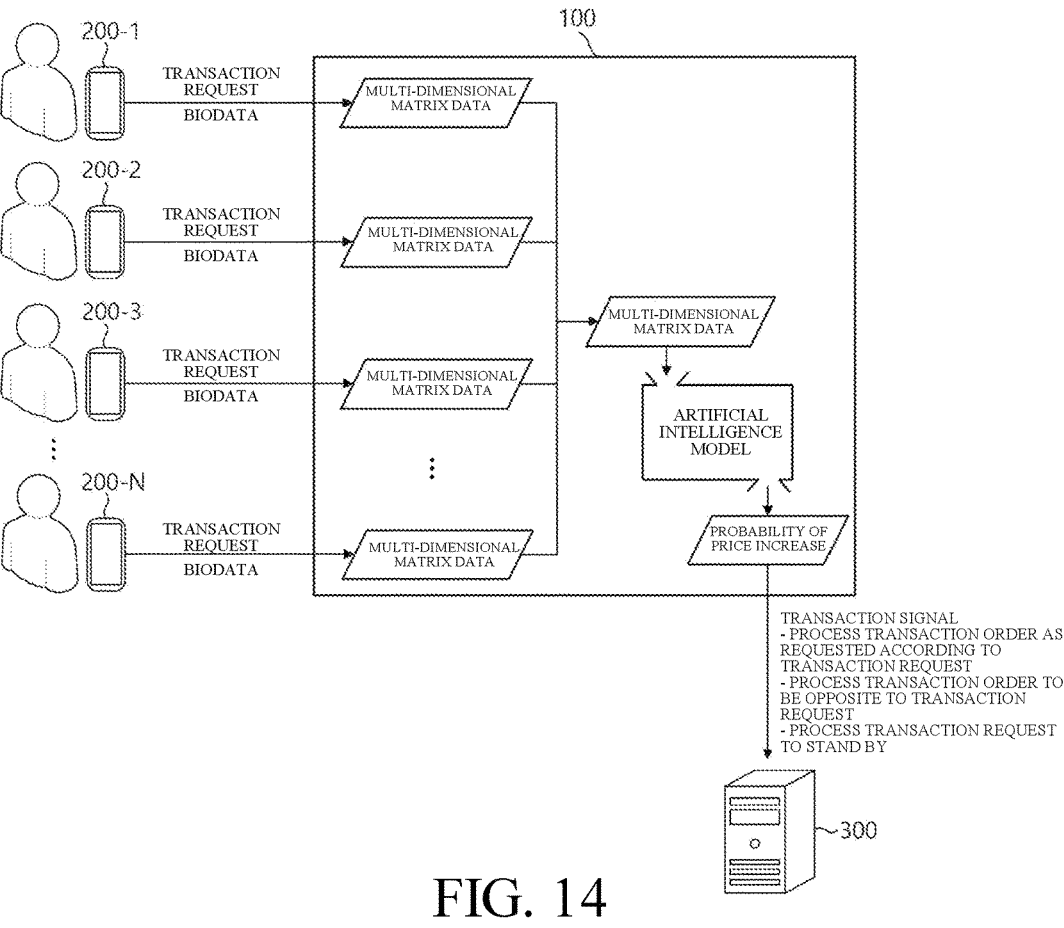
FIG. 14 is a view illustrating a process of performing a financial product transaction method for a plurality of traders according to a third embodiment, in various exemplary embodiments.

FIG. 13 is a flowchart for explaining a third embodiment of a financial product transaction method using an artificial intelligence model according to still another exemplary embodiment of the present invention and FIG. 14 is a view illustrating a process of performing a financial product transaction method for a plurality of traders according to a third embodiment, in various exemplary embodiments.

Here, it is described that a financial product transaction method using an artificial intelligence model of FIGS. 13 and 14 is performed by a computing device 100, but is not limited thereto and may be independently performed in a trader terminal 200 as the trader terminal 200 executes software provided from the computing device 100.

Referring to FIGS. 13 and 14, in step S610, the computing device 100 may simultaneously acquire transaction requests for a financial product from a plurality of traders at a predetermined time. For example, the computing device 100 is connected to trader terminals 200 of the plurality of traders through a network 400 to provide UIs to the trader terminals 200. The computing device 100 may acquire simultaneously the transaction requests for the same financial product from the plurality of traders at a predetermined transaction time (for example, 10 minutes after the opening the financial product trading floor) through the UIs. However, it is not limited thereto. If the predetermined transaction time is 10 minutes after the opening of the financial product trading floor, the computing device 100 may acquire the transaction requests for the specific financial product from the plurality of traders within a time range from the opening of the financial product trading floor to 10 minutes from the opening and freely modify the transaction requests (for example, change the transaction mode or change the transaction quantity) within the time range.

In step S620, the computing device 100 may collect biodata about the plurality of traders who inputs the transaction request at the predetermined transaction time in step S610, for a predetermined period.

First, the computing device 100 may be connected to trader terminals 200 of the plurality of traders through the network 400 and may provide information about a financial product to the trader terminals 200.

In various embodiments, the computing device 100 may collectively provide information about the financial products to the plurality of traders before a predetermined time in the past (for example, approximately 2 minutes) as of a previously determined transaction time. For example, when the transaction time is set to 10 minutes after the opening of the financial product trading floor, the computing device 100 may provide information about the financial products to the plurality of traders about 2 minutes before the transaction time, that is, 8 minutes after the opening of the financial product trading floor.

Thereafter, the computing device 100 may collect biodata from the plurality of traders (who acquires the transaction requests) for a predetermined time (10 minutes after the opening of the financial product trading floor, that is, for about 2 minutes) from the time when the information about the financial products is provided to the plurality of traders (8 minutes after the opening of the financial product trading floor). Here, the biodata collecting method performed by the computing device 100 may be implemented to be the same as or similar to the biodata collecting method performed in step S120 of FIG. 3, but is not limited thereto.

In step S630, the computing device 100 may calculate the probability of price increase for the financial product using at least one of the biodata of the plurality of traders collected in step S620, the transaction requests for the financial product that are simultaneously acquired from the plurality of traders, transaction history data, and test result data. For example, the computing device 100 may generate multi-dimensional matrix data using at least one of the biodata of the plurality of traders, the transaction requests for the financial product that are simultaneously acquired from the plurality of traders, the transaction history data, and the test result data. The computing device 100 may input the generated multi-dimensional matrix data to the previously trained artificial intelligence model (for example, the fourth artificial intelligence model) as input data to extract result data about the probability of price increase of the financial product.

In step s640, the computing device 100 may determine the processing mode for the plurality of transaction requests that is simultaneously acquired from the plurality of traders, based on the probability of price increase of the financial product calculated in step S630. For example, the computing device 100 may determine the processing mode for the plurality of transaction requests that is simultaneously acquired from the plurality of traders to the selling processing if the probability of price increase is lower than a predetermined first reference value (for example, 0.35). For example, the computing device 100 may determine the processing mode for the plurality of transaction requests that is simultaneously acquired from the plurality of traders to the buying processing if the probability of price increase is equal to or higher than a second reference value (0.65). The computing device 100 may determine the processing mode for the plurality of transaction requests that is simultaneously acquired from the plurality of traders to the holding process if the probability of price increase is equal to or higher than the first reference value and lower than the second reference value range.

In step S650, the computing device 100 may output the transaction signals for the plurality of transaction requests according to the processing mode determined in step S640. For example, when the probability of price increase for the financial product is lower than 0.35 so that the processing mode for the plurality of transaction requests is determined to be the selling processing, the computing device 100 normally processes the selling request among the plurality of transaction request and reversely processes the buying request to output a selling signal to sell the financial product.

In the meantime, when the probability of price increase for the financial product is equal to or higher than 0.65 so that the processing mode for the plurality of transaction requests is determined to be the buying processing, the computing device 100 normally processes the buying request among the plurality of transaction request and reversely processes the selling request to output a buying signal to buy the financial product. Hereinafter, a method for automatically outputting a transaction signal according to a buying request probability and a selling request probability of each of the plurality of traders will be described with reference to FIGS. 15 and 16.

Figure 15:
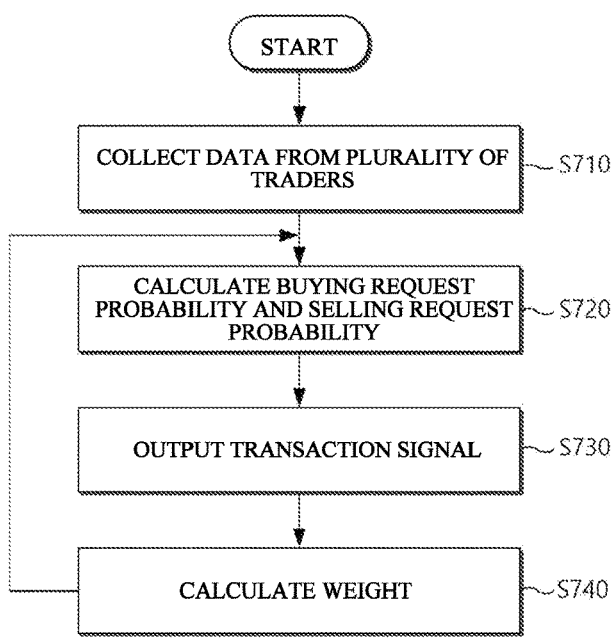
FIG. 15 is a flowchart for explaining a method for outputting a transaction signal by calculating a buying request probability and a selling request probability of each of a plurality of traders, in various exemplary embodiments.
Figure 16:
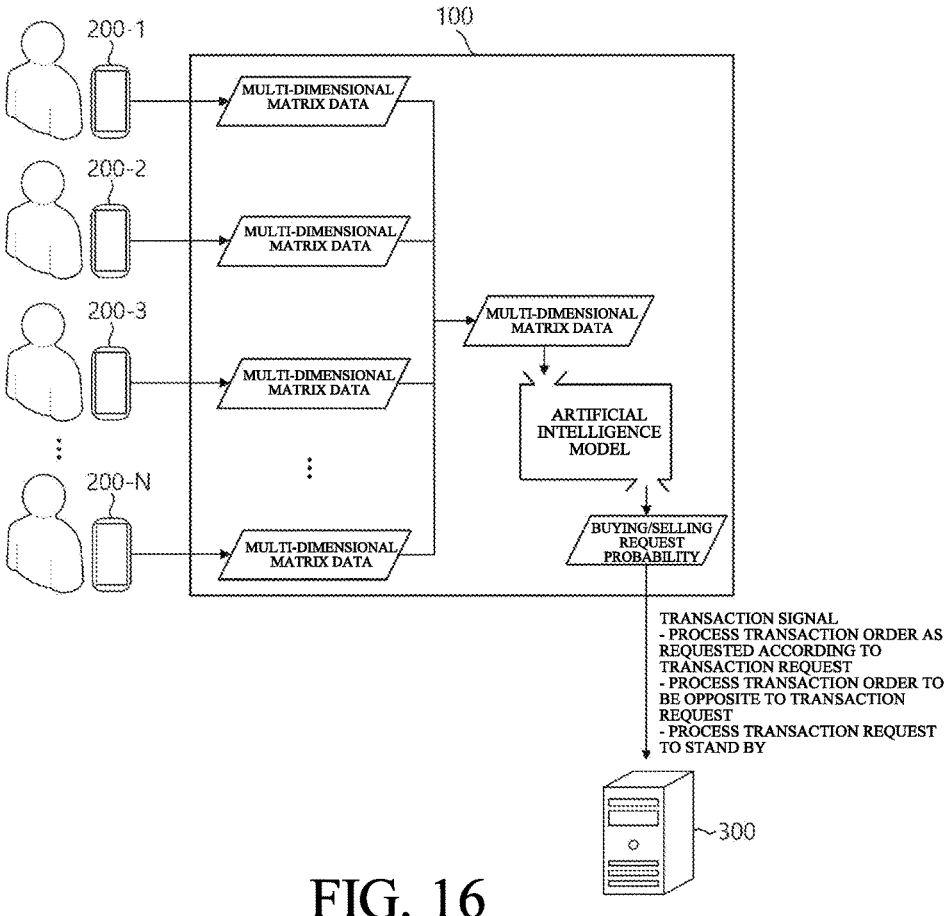
FIG. 16 is a view illustrating a process of performing a method for outputting a transaction signal by calculating a buying request probability and a selling request probability of each of a plurality of traders, in various exemplary embodiments.

FIG. 15 is a flowchart for explaining a method for outputting a transaction signal by calculating a buying request probability and a selling request probability of each of a plurality of traders, in various exemplary embodiments and FIG. 16 a view illustrating a process of performing a method for outputting a transaction signal by calculating a buying request probability and a selling request probability of each of a plurality of traders, in various exemplary embodiments.

Here, it is described that the method for outputting a transaction signal by calculating a buying request probability and a selling request probability of FIGS. 15 and 16 is performed by a computing device 100, but is not limited thereto and may be independently performed in a trader terminal 200 as the trader terminal 200 executes software provided from the computing device 100.

Referring to FIGS. 15 and 16, in step S710, the computing device 100 may collect data about traders (for example, biodata, transaction history data, test result data, and financial data) from a plurality of traders. For example, the computing device 100 may collect the data about the plurality of traders through sensors that are separately provided in trader terminals 200 of the plurality of traders. However, it is not limited thereto, but various methods, such as a method for directly receiving data from each of the plurality of traders may be applied.

In step S720, the computing device 100 may calculate a buying request probability and a selling request probability of each of the plurality of traders for a financial product using biodata of each of the plurality of traders. For example, the computing device 100 inputs biodata of each of the plurality of traders to a previously trained artificial intelligence model (for example, a fifth artificial intelligence model) to calculate a buying request probability and a selling request probability of each of the plurality of traders.

Here, the fifth artificial intelligence model may be a model that is trained in advance with a transaction request (buying or selling request) acquired from the plurality of traders and biodata about each of the traders at the time when the transaction request is acquired, as learning data. Further, the structure and the learning method of the third artificial intelligence model may be implemented to be the same as or similar to the first artificial intelligence model and the second artificial intelligence model.

In step S730, the computing device 100 may output a transaction signal for the financial product using the buying request probability and the selling request probability calculated in step S720. For example, the computing device 100 calculates an average of the buying request probability and an average of the selling request probability calculated for each of the plurality of traders and compares the averages to output the transaction signal for the financial product.

In step S740, the computing device 100 may determine a weight to be assigned to each of the plurality of traders based on the transaction signal output in step S730 and a rate of return according to the transaction signal. For example, the computing device 100 may output a first transaction signal (for example, a buying signal) based on the first biodata of each of the plurality of traders and may buy a specific financial product according to the first transaction signal and may calculate a rate of return for the bought specific financial product.

Thereafter, the computing device 100 assigns a weight to each of the plurality of traders based on the calculated rate of return. When the rate of return is equal to or higher than a reference rate of return, among the plurality of traders, a trader who was predicted to make a buying request is assigned with a larger weight than a trader who was predicted to make a selling request. For example, the computing device 100 may assign a weight between 1 and 2, to the trader who was predicted to make a buying request, among the plurality of traders The computing device 100 may assign a weight between 0 and 1 to the trader who was predicted to make a selling request.

That is, the computing device 100 outputs a buying signal for the specific financial product based on the buying request probability and the selling request probability of the plurality of traders. When a large profit is made by buying the specific financial product, the computing device 100 is set to assign a larger weight to a trader who contributed to outputting the buying signal so that data of a trader who helped generate the profits is given more weight than the data of a trader who hindered the profits.

Further, when the selling signal for the specific financial product was output based on the buying request probability and the selling request probability of the plurality of traders and thus the specific financial product was bought, but suffered a loss, the computing device 100 may set the data of the trader who has decided not to incur the losses will be given a higher weight relatively. For example, the computing device 100 may assign a lower weight to a trader who contributed to outputting the buying signal to lower the weight of the data of the trader who affects the losses and assign a higher weight to a trader who contributed to preventing the buying signal from being output.

At this time, the magnitude of the weight may be determined depending on a size of the probability calculated according to the above method. For example, when the buying signal is output based on the biodata of each of the plurality of traders and a profit that is larger than a predetermined size is generated as a result of buying the specific financial product according to the buying signal, the computing device 100 is set to assign a weight between 1 and 2 to a trader who was predicted to make a buying request, among a plurality of traders. The computing device 100 is set to assign a relatively larger weight to a trader having a higher buying request probability, among traders who were predicted to make a buying request, than to a trader having a lower buying request probability.

In various embodiments, the computing device 100 may determine or correct a weight for each of the plurality of traders based on the transaction history data of each of the plurality of traders.

The weight is assigned as described above to place a larger weight on a decision of a trader who accurately predicted a buying or selling timing, that is, a trader having a high reliability. However, if a low weight is assigned to a trader who accurately predicted the buying or selling timing on average to have a high rate of return due to the reason that the prediction results were not good once or twice, there is a problem in that the reliability of the overall results may be lowered.

Accordingly, the computing device 100 outputs a transaction signal using a buying request probability and a selling request probability calculated based on the biodata and assigns the weight for each of the plurality of traders based on the result according to the output transaction signal. In that case, the assigned weight is adjusted by considering a basic skill of each of the plurality of traders, that is, a rate of return (or a winning rate) of each of the plurality of traders to solve the above-described problem.

In various embodiments, the computing device 100 may calculate an outcome for each of the plurality of traders based on the transaction history data of each of the plurality of traders and determines a weight to be assigned to each of the plurality of traders, based on the calculated outcome. For example, the computing device 100 calculates an outcome of each of the plurality of traders using rate of returns for a predetermined period (for example, one week) of the plurality of traders and assigns a relatively larger weight to a trader having a high outcome than a trader having a low outcome, based on the calculated outcome.

Thereafter, the computing device 100 performs again steps S710 to S730 to output a second transaction signal using second biodata of each of the plurality of traders and in this case. The second transaction signal may be output using a weight assigned to each of the plurality of traders, based on the first transaction signal. For example, the computing device 100 assigns the determined weight to the buying request probability and the selling request probability calculated using the second biodata and may output the second transaction signal using the weight-assigned buying request probability and the weight-assigned selling request probability.

Thereafter, the computing device 100 may update the weight based on a result (rate of return) according to the second transaction signal. The computing device 100 may apply a third transaction signal that is output after the second transaction signal using the updated weight.

The above-described financial product transaction method using an artificial intelligence model has been described with reference to the flowchart illustrated in the drawing. For a simple description, the financial product transaction method using an artificial intelligence model has been illustrated as a series blocks to be described, but the present invention is not limited to the order of the blocks and some blocks may be performed in different orders from the orders illustrated and described in the specification or simultaneously performed. Further, a new block that has not described in the present specification and the drawings may be added or some blocks may be deleted or modified.

The exemplary embodiments of the present invention have been described with reference to the accompanying drawings, but those skilled in the art will understand that the present disclosure may be implemented in another specific form without changing the technical spirit or an essential feature thereof. Therefore, it should be understood that the above-described exemplary embodiments are illustrative in all aspects and do not limit the present disclosure.

What is claimed is:

1. A method using an artificial intelligence (AI) model executed by a computing device for processing a transaction order, the method comprising:

collecting data about a plurality traders for a predetermined period, the collected data including biodata about the plurality of traders, the biodata including at least one of electroencephalography (EEG) data measured by an EEG sensor and brain oxygen saturation data measured by a functional near-infrared spectroscopy (fNIRS) sensor;

acquiring a transaction request for a financial product from a trader of the plurality of traders;

determining a processing mode for the transaction request by analyzing the collected data using the AI model; and outputting a transaction signal corresponding to the determined processing mode for the transaction request, wherein the processing mode is determined by inputting, to the AI model, the biodata of the trader and extracting result data about the processing mode for the transaction request, the biodata being collected periodically from a time that a financial product market corresponding to the financial product opens and being input to the AI model at a time when the transaction request for the financial product is acquired, wherein the AI model is trained with learning data comprised of biodata collected at a time when each of the plurality of traders transmits a transaction request, a transaction signal output according to the transaction request of each of the plurality of traders, and a rate of return according to the output transaction signal of each of the plurality of traders, wherein the collected data further includes biodata according to a state of each of the plurality of traders, the state of any one of the plurality of traders including at least one of perception, learning, memory, attention, motivation, valence, arousal, happiness, fear, relaxation, excitement, introvert/extrovert personality, and stress, wherein the processing mode is determined based on the state of the trader at the time when the transaction request for the financial product is acquired by further extracting result data about the state of the trader, and wherein the AI model is trained with the learning data being further comprised of the biodata according to state of each of the plurality of traders.

2. The method of claim 1, wherein the data about the trader further includes test result data about tests conducted on the trader before the opening of the financial product market, and transaction history data including at least one of the trader's past financial product transaction data, rate of return data, and personal information data, and wherein the processing mode is determined by further inputting, to the AI model, at least one of the transaction history data and the test result data.

3. The method of claim 1, wherein the processing mode is determined by further inputting, to the AI model, financial data including at least one of technical indicators, financial statements, performance, news, and chart patterns.

4. The method of claim 1, wherein the determining of the processing mode includes:

calculating a probability of price increase of the financial product using the collected data, the predetermined period beginning from a time when information about the financial product is provided to the plurality of traders; and correcting the determined processing mode for the transaction request, based on the calculated probability of price increase of the financial product.

5. The method of claim 1, wherein the determining of the processing mode includes:

calculating an expected rate of return of the trader using at least one of the biodata about the trader, transaction history data, test result data, and financial data, and correcting the determined processing mode for the transaction request based on the calculated expected rate of return, wherein the transaction history data includes at least one of the trader's past financial product transaction data, the rate of return data, and personal information data, wherein the test result data includes data about tests conducted on the trader before the opening of the financial product market, and wherein the financial data includes at least one of technical indicators, financial statements, performance, news, and chart patterns.

6. The method of claim 1, wherein the predetermined period begins from a time when information about the financial product is provided to the plurality of traders;

wherein the determining of the processing mode includes:

generating multi-dimensional matrix data using the collected biodata of the plurality of traders;

inputting the multi-dimensional matrix data to the AI model; and extracting result data about a probability of price increase of the financial product, and wherein the AI model is trained with learning data comprised of information about a plurality of financial products, a plurality of biodata collected from the plurality of traders at the time when the information about the plurality of financial products is provided to the plurality of traders, a plurality of multi-dimensional matrix data generated using the plurality of biodata, and a price change amount of the plurality of financial products.

7. The method of claim 6, wherein the determining of the processing mode further includes correcting the determined processing mode for the transaction request using biodata about the trader collected for a past predetermined period beginning from a time when the transaction request for the financial product is acquired from the trader.

8. The method of claim 7, wherein the correcting the determined processing mode for the transaction request includes:

extracting result data about a state of the trader by inputting, to the AI model, the biodata about the trader for the past predetermined period; and correcting the determined processing mode for the transaction request based on the state of the trader, and wherein the AI model is trained with the learning data being further comprised of the biodata according to a state of each of the plurality of traders as learning data.

9. The method of claim 6, wherein the collecting biodata from the plurality of traders includes providing, to the plurality of traders, information about an occurred event about the financial product in response to a sensing of the occurrence of the event and collecting biodata from the plurality of traders for a predetermined period from a time that the information about the occurred event is provided to the plurality of traders, and wherein the determining of the processing mode for the transaction request uses the probability of price increase of the financial product and includes:

determining an attribute of the occurred event using the collected biodata of the plurality of traders and correcting the determined processing mode for the transaction request based on the determined attribute.

10. The method of claim 1, wherein the collected data about the trader further includes transaction history data including at least one of the trader's past financial product transaction data, rate of return data, and personal information data, and test result data about tests conducted on the trader before the opening of the financial product market, wherein the acquiring of the transaction request for the financial product includes acquiring simultaneously the transaction request for the financial product from a plurality of traders at a predetermined time, wherein the predetermined period begins from a time when information about the financial product is provided to the plurality of traders, and wherein the determining of the processing mode includes:

generating multi-dimensional matrix data using at least one of the collected biodata of the plurality of traders, a transaction request for the financial product that is simultaneously acquired from the plurality of traders, the transaction history data, and the test result data;

inputting the multi-dimensional matrix data to the AI model; and extracting result data about a probability of price increase of the financial product.

11. The method of claim 1, wherein the outputting of the transaction signal includes:

calculating a buying request probability and a selling request probability of each of the plurality of traders for a first financial product using data about each of the plurality of traders; and automatically outputting a transaction signal for the first financial product using the calculated buying request probability and the calculated selling request probability.

12. The method of claim 11, wherein the outputting automatically of the transaction signal includes:

determining a weight to be assigned to each of the plurality of traders based on a rate of return according to a first transaction signal output using first data about each of the plurality of traders; and outputting a second transaction signal using second data about each of the plurality of traders, the determined weight being assigned to the selling request probability and the buying request probability calculated using the second data and the second transaction signal being automatically output using the buying request probability assigned with the weight and the selling request probability assigned with the weight.

13. A server using an artificial intelligence (AI) model, the server comprising:

a processor coupled to a network interface;

a memory; and a computer program that is loaded in the memory and is executed by the processor, wherein the computer program includes a sequence of instructions for processing a transaction order by:

collecting data about a plurality traders for a predetermined period, the collected data including biodata about the plurality of traders, the biodata including at least one of electroencephalography (EEG) data measured by an EEG sensor and brain oxygen saturation data measured by a functional near-infrared spectroscopy (fNIRS) sensor;

acquiring a transaction request for a financial product from a trader of the plurality of traders;

determining a processing mode for the transaction request by analyzing the collected data using an artificial intelligence (AI) model; and outputting a transaction signal corresponding to the determined processing mode for the transaction request, wherein the processing mode is determined by inputting, to the AI model, the biodata of the trader and extracting result data about the processing mode for the transaction request, the biodata being collected periodically from a time that a financial product market corresponding to the financial product opens and being input to the AI model at a time when the transaction request for the financial product is acquired, wherein the AI model is trained with learning data comprised of biodata collected at a time when each of the plurality of traders transmits a transaction request, a transaction signal output according to the transaction request of each of the plurality of traders, and a rate of return according to the output transaction signal of each of the plurality of traders, wherein the collected data further includes biodata according to a state of each of the plurality of traders, the state of any one of the plurality of traders including at least one of perception, learning, memory, attention, motivation, valence, arousal, happiness, fear, relaxation, excitement, introvert/extrovert personality, and stress, wherein the processing mode is determined based on the state of the trader at the time when the transaction request for the financial product is acquired by further extracting result data about the state of the trader, and wherein the AI model is trained with the learning data being further comprised of the biodata according to the state of each of the plurality of traders.

14. A non-transitory computer readable recording medium storing a computer program including instructions for processing a transaction order using an artificial intelligence (AI) model executed by a computing device, the computer program causing the computing device to:

collect data about a plurality traders for a predetermined period, the collected data including biodata about the plurality of traders, the biodata including at least one of electroencephalography (EEG) data measured by an EEG sensor and brain oxygen saturation data measured by a functional near-infrared spectroscopy (fNIRS) sensor;

acquire a transaction request for a financial product from a trader of the plurality of traders;

determine a processing mode for the transaction request by analyzing the collected data using the AI model; and output a transaction signal corresponding to the determined processing mode for the transaction request, wherein the processing mode is determined by inputting, to the AI model, the biodata of the trader and extracting result data about the processing mode for the transaction request, the biodata being collected periodically from a time that a financial product market corresponding to the financial product opens and being input to the AI model at a time when the transaction request for the financial product is acquired, wherein the AI model is trained with learning data comprised of biodata collected at a time when each of the plurality of traders transmits a transaction request, a transaction signal output according to the transaction request of each of the plurality of traders, and a rate of return according to the output transaction signal of each of the plurality of traders, wherein the collected data further includes biodata according to a state of each of the plurality of traders, the state of any one of the plurality of traders including at least one of perception, learning, memory, attention, motivation, valence, arousal, happiness, fear, relaxation, excitement, introvert/extrovert personality, and stress, wherein the processing mode is determined based on the state of the trader at the time when the transaction request for the financial product is acquired by further extracting result data about the state of the trader, and wherein the AI model is trained with the learning data being further comprised of the biodata according to the state of each of the plurality of traders.

\* \* \* \* \*